United States Patent [19]
Froimowitz et al.

[11] Patent Number: 5,821,386
[45] Date of Patent: Oct. 13, 1998

[54] COMPOUNDS FOR TREATING COCAINE ABUSE

[75] Inventors: Mark Froimowitz, Newton; Kuo-Ming Wu, Acton, both of Mass.

[73] Assignee: Allelix-Pharm-Eco L.P., Lexington, Mass.

[21] Appl. No.: 911,864

[22] Filed: Aug. 15, 1997

[51] Int. Cl.$^6$ .................................................. C07C 211/42
[52] U.S. Cl. ........................ 564/308; 558/418; 558/422
[58] Field of Search ............................. 564/308; 558/418, 558/422

[56] References Cited

U.S. PATENT DOCUMENTS

5,639,913  6/1997  Lidor et al. .............................. 564/304

FOREIGN PATENT DOCUMENTS

0076669   4/1978  European Pat. Off. .
2339715   2/1975  Germany .
WO95/18617 7/1995  WIPO .

OTHER PUBLICATIONS

S. Rosonzweig–lipson et al., "Stereoselective Behavorial Effects of Lu 19–005 in Monkeys: Relation to Binding at Cocaine Recognition Sites," *Psychopharmacology*, 107: 186–194 (1992).

K. P. Bogeso, et al., 3–Phenyl–1–Indanamines Potential Antidepressant Activity and Potent inhibition of Dopamine, Norepinephrine and Serotonin Uptake, *J. Med. Chem.*, 28:1817–1828 (1985).

S. Izenwasser, et al., "Differential Relationships Among Dopamine Transporter Affiniities and Stimulant Potencies of Various Uptake inhibitors," *European Journal of Pharmacology*, 263:277–283 (1994).

N. Tomita, "Structure–Actuvuty Relatonaships of dopamine–a nd Norepinephrine–Uptake Inhibitors," *Chem. Pharm. Bull.* 38(6):1563–1569 (1990).

M. Froimowitz, et al., "Slow Onset, Long Lasting Dopamine Reuptake Blockers as Potential Medications for the Treatment of Cocaine Abuse," 1996 Annual Meeting, Washington, D.C., Nov. 16–21, 1996, Abstract, Mail Date: Aug. 18, 1996.

M. Froimowitz, et a;., "Effects of a Slow–Onset, Long–Acting Dopamine Reuptake Blocker on Cocaine Self–Administration and on Nucleus Accumbers Dopamine," Society for Neuroscience Abstracts, vol. 23, Part 1, 27$^{th}$ Annual Meeting, New Orleans, LA, Oct. 25–30, 1997, Mail Date: Aug. 25, 1997.

Agenda for oral presentation at the National Instistute in Drug Abuse National Instistutes of Health Meeting entitled, "Cocaine Medications–Better Treatment Through chemistry," Scientific Meeting at the National Instistute on Drug Abuse, Apr. 29–30, 1996.

Elliot L. Gardner, et al., Poster presented at meetings of the College on Problems of Drug Dependence, Nashville, Tennessee, Jun. 1997.

*Primary Examiner*—Richard L. Rayomnd
*Attorney, Agent, or Firm*—Hamilton, Brook, Smith & Reynolds, P.C.

[57] ABSTRACT

Disclosed are novel compounds which are dopamine reuptake blockers for treating cocaine abuse. The compounds are represented by the following structural formula:

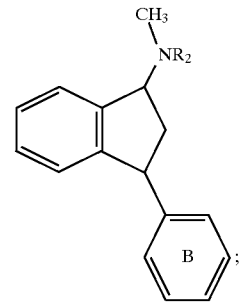

R2 is n-propyl, iso-propyl, n-butyl, sec-butyl, or tert-butyl. Phenyl Ring B is unsubstituted or substituted with one, two or three substituents.

8 Claims, 19 Drawing Sheets

COMPOUNDS FOR TREATING COCAINE ABUSE

GOVERNMENT FUNDING

This invention was made with Government support under Contract No. NO1DA-4-8313 awarded by the National Institute on Drug Abuse. The Government has certain rights in the invention.

RELATED APPLICATIONS

This application claims priority to U.S. Ser. No. 60/024,099, filed Aug. 16, 1996, the teachings of which are incorporated herein by reference.

BACKGROUND OF THE INVENTION

Drugs which block the reuptake of dopamine have many uses, including the treatment of individuals who abuse cocaine. It is believed that the abuse potential of cocaine is a result of its short onset of action (on the order of seconds) and its short duration of action (on the order of minutes). A slow onset, long duration dopamine reuptake blocker would have greatly reduced abuse potential and could be used as a treatment for chronic cocaine use.

Many dopamine reuptake blockers are non-selective, and, for example, can inhibit the reuptake of other neurotransmittors such as serotonin and/or norepinephrine. Dopamine reuptake blockers which inhibit the reuptake of other neurotransmittors or bind other receptor sites have pharmacological profiles which differ from the pharmacological profile of cocaine. Preferred dopamine reuptake inhibitors for use in treating cocaine abuse have pharmacological profiles resembling the pharmacological profile of cocaine. Dopamine reuptake inhibitors which block the reuptake of other neurotransmittors also have the potential to cause undesirable side-effects. Consequently, there is a need to identify slow-onset long-duration dopamine reuptake blockers which do not block the reuptake of other neurotransimittors.

SUMMARY OF THE INVENTION

The present invention is directed to novel N,N-dialkyl 3-phenyl-1-indamines, which are slow-onset, long-lasting dopamine reuptake blockers. The use of N,N-dialkyl 3-phenyl-1-indamines for treating individuals who abuse cocaine, individuals with Parkinson's disease and individuals with attention deficit hyperactivity disorder are disclosed in co-pending U.S. Application, entitled SLOW-ONSET, LONG-LASTING DOPAMINE REUPTAKE BLOCKERS U.S. application Ser. No. 08/911,778, filed on Aug. 15, 1997, the entire teachings of which are incorporated herein by reference.

One embodiment of the present invention is a novel compound represented by Structural Formula (I):

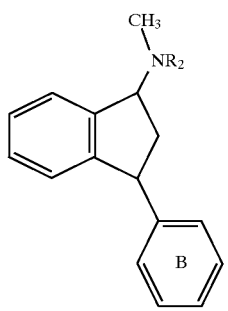

Ring B is unsubstituted or substituted with one, two or three substituents other than hydrogen. Suitable substituents include halogen, an alkyl group, a substituted alkyl group, hydroxy, (lower alkyl)—O—, (substituted lower alkyl)—O—, —CN, —NO$_2$, amine, (lower alkyl) amine, (substituted lower alkyl) amine, (di-lower alkyl) amine and (substituted di-lower alkyl) amine.

R2 is n-propyl, iso-propyl, n-butyl, sec-butyl, or tert-butyl, preferably n-propyl.

The compound represented by Structural Formula (I) preferably has the trans stereochemistry.

Another embodiment of the present invention is a compound represented by Structural Formula (I), wherein R2 is ethyl, and Phenyl Ring B is substituted in the meta and para positions relative to carbon atom bonded to the indane group with —Cl (Compound 3).

Another embodiment is a compound represented by Structural Formula (I), wherein R2 is an aralkyl group (—(CH$_2$)$_n$-aryl or —(CH$_2$)$_n$-(substituted aryl)). Phenyl Ring B is as described for Structural Formula (I) and n is an integer from one to about three. The compound preferably has the trans stereochemistry.

The N-methyl-N-(n-propyl) 3-phenyl-1-indamines of the present invention, e.g., Compound 2, are superior, when used to treat cocaine abuse, to the corresponding N,N-dimethyl 3-phenyl-1-indamine, Compound 1, because Compound 1 selectively inhibits serotonin and norepinephrine reuptake (Example 5). In contrast, Compound 2 shows reduced inhibition of serotonin and norepinephrine reuptake and more closely resembles the pharmacological profile of cocaine (Example 5). Thus, N-methyl-N-(n-propyl) 3-phenyl-1-indamines such as Compound 2, are expected to be more efficacious and cause fewer side effects than the corresponding N,N-dimethyl compounds when substituted for cocaine during the treatment of individuals

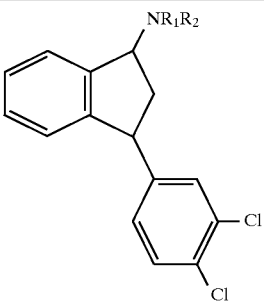

| | | |
|---|---|---|
| 1 | R1 = methyl | R2 = methyl |
| 2 | R1 = methyl | R2 = n-propyl |
| 3 | R1 = methyl | R2 = ethyl |

-continued

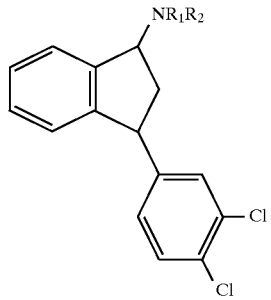

| | | |
|---|---|---|
| 4 | R1 = —H | R2 = ethyl |
| 5 | R1 = —H | R2 = methyl |
| 6 | R1 = —H | R2 = t-butyl |
| 7 | R1 = methyl | R2 = t-butyl | for cocaine abuse. It has also been found that the N-ethyl-N-butyl 3-phenyl-1-indamines (e.g., Compound 7) lock the effects of cocaine in laboratory mice while reducing locomotor activity (Examples 2 and 3). Thus, N-ethyl-N-butyl 3-phenyl-1-indamines such as Compound 7 can be used to treat individuals who abuse cocaine without causing the stimulatory effects of cocaine.

DETAILED DESCRIPTION OF THE INVENTION

Figure 1:
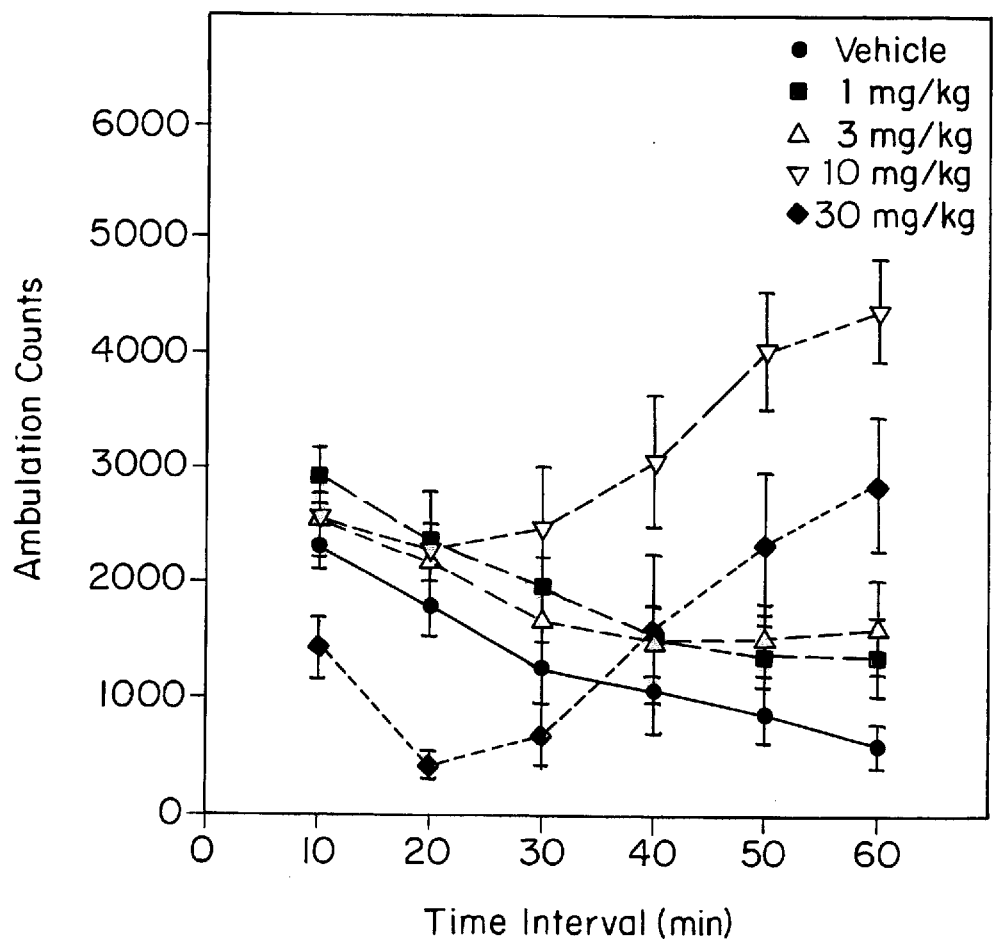
FIG. 1 is a graph showing the number of ambulation counts resulting from the stimulation of locomotor activity in mice over time by the administration of 1) vehicle; 2) 1 mg/kg of Compound 1; 3) 3 mg/kg of Compound 1; 4) 10 mg/kg of Compound 1; and 5) 30 mg/kg of Compound 1.
Figure 2:
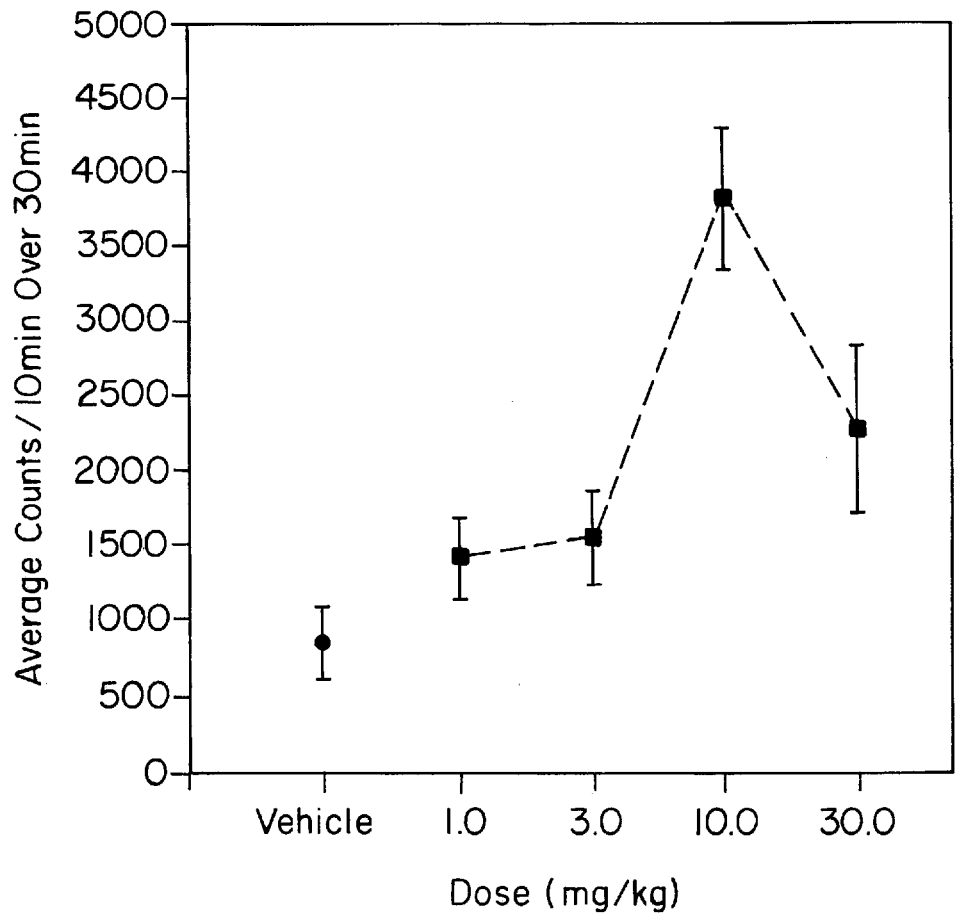
FIG. 2 is a graph showing the average number of ambulation counts/10 minutes over 30 minutes resulting from the stimulation of locomotor activity in mice versus the dosage of Compound 1 administered to the mice.
Figure 3:
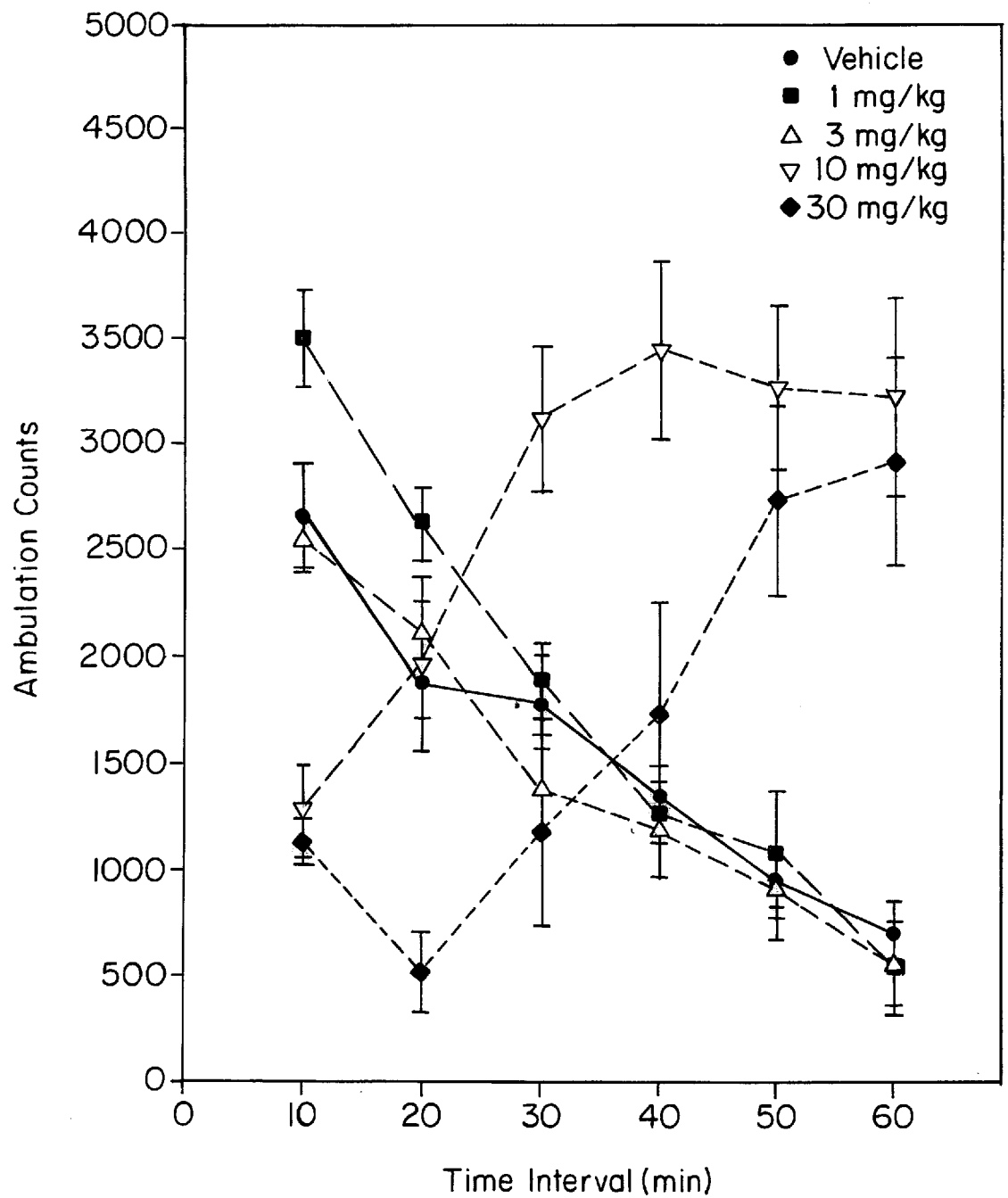
FIG. 3 is a graph showing the number of ambulation counts resulting from the stimulation of locomotor activity in mice over time by the administration of 1) vehicle; 2) 1 mg/kg of Compound 2; 3) 3 mg/kg of Compound 2; 4) 10 mg/kg of Compound 2; and 5) 30 mg/kg of Compound 2.
Figure 4:
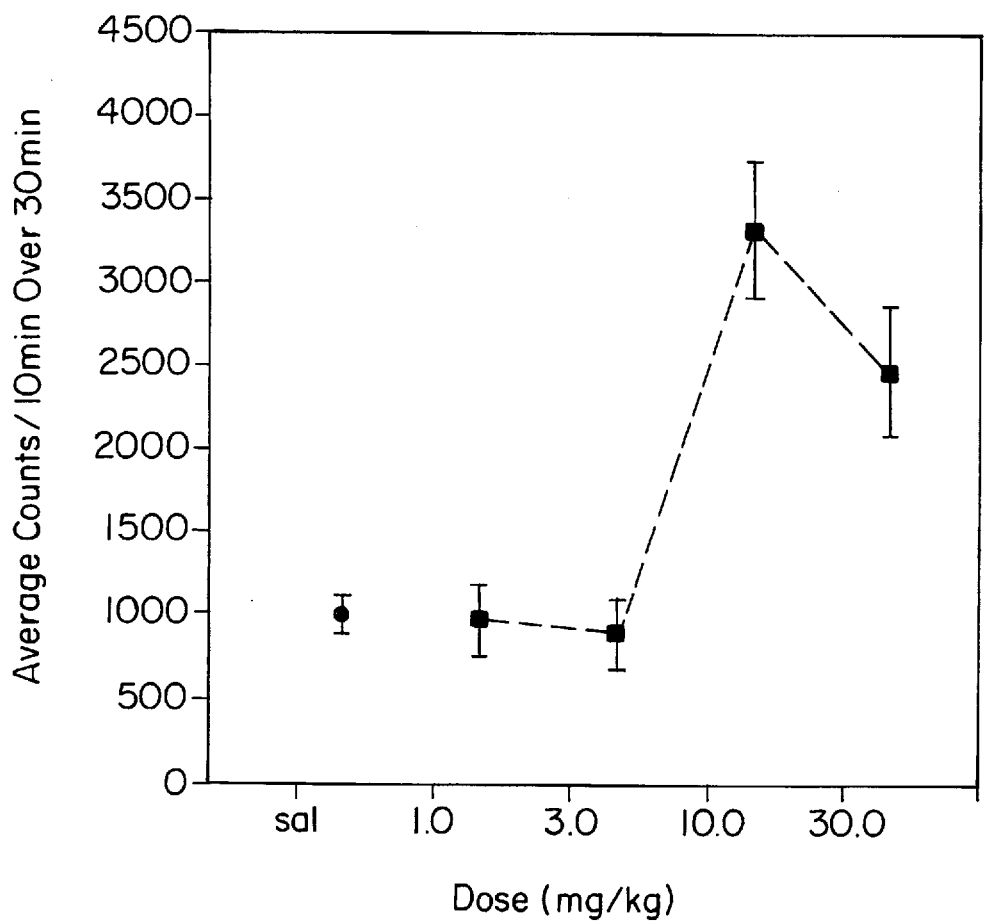
FIG. 4 is a graph showing the average number of ambulation counts/10 minutes over 30 minutes resulting from the stimulation of locomotor activity in mice versus the dosage of Compound 2 administered to the mice.
Figure 5:
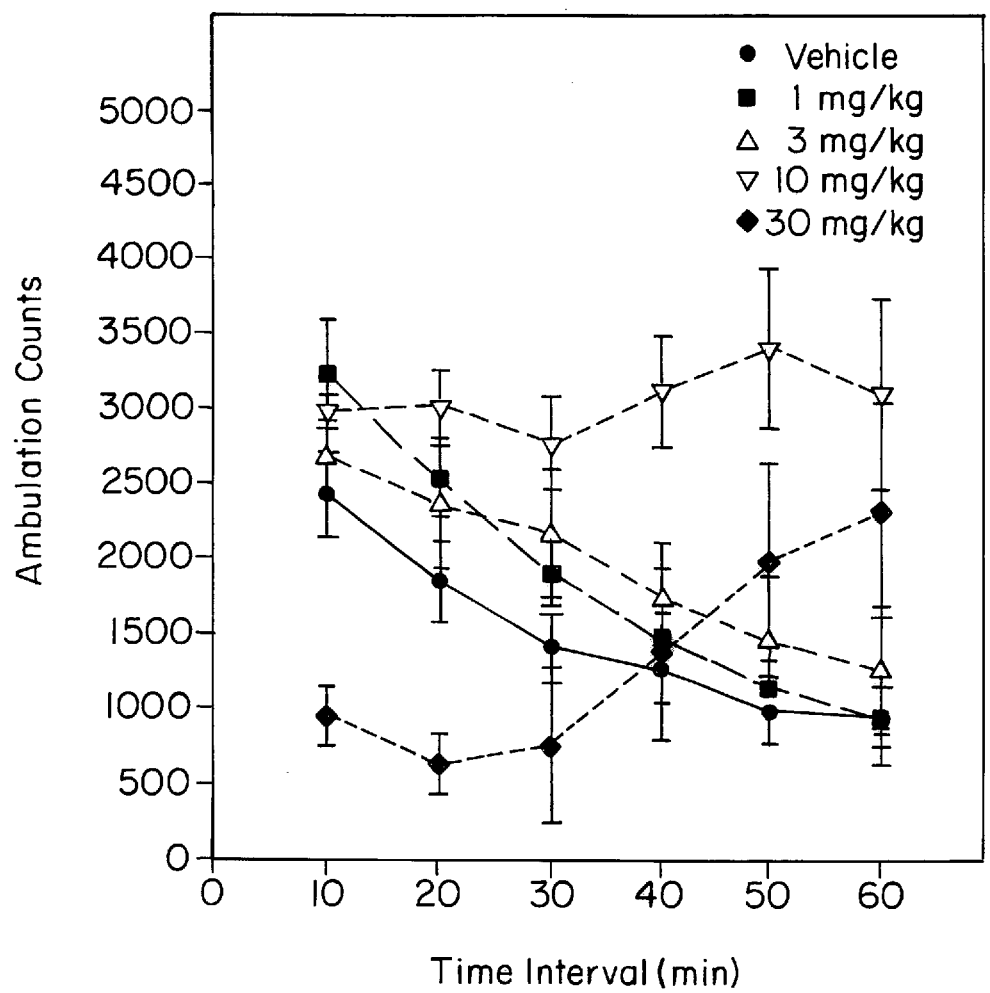
FIG. 5 is a graph showing the number of ambulation counts resulting from the stimulation of locomotor activity in mice over time by the administration of 1) vehicle; 2) 1 mg/kg of Compound 3; 3) 3 mg/kg of Compound 3; 4) 10 mg/kg of Compound 3; and 5) 30 mg/kg of Compound 3.
Figure 6:
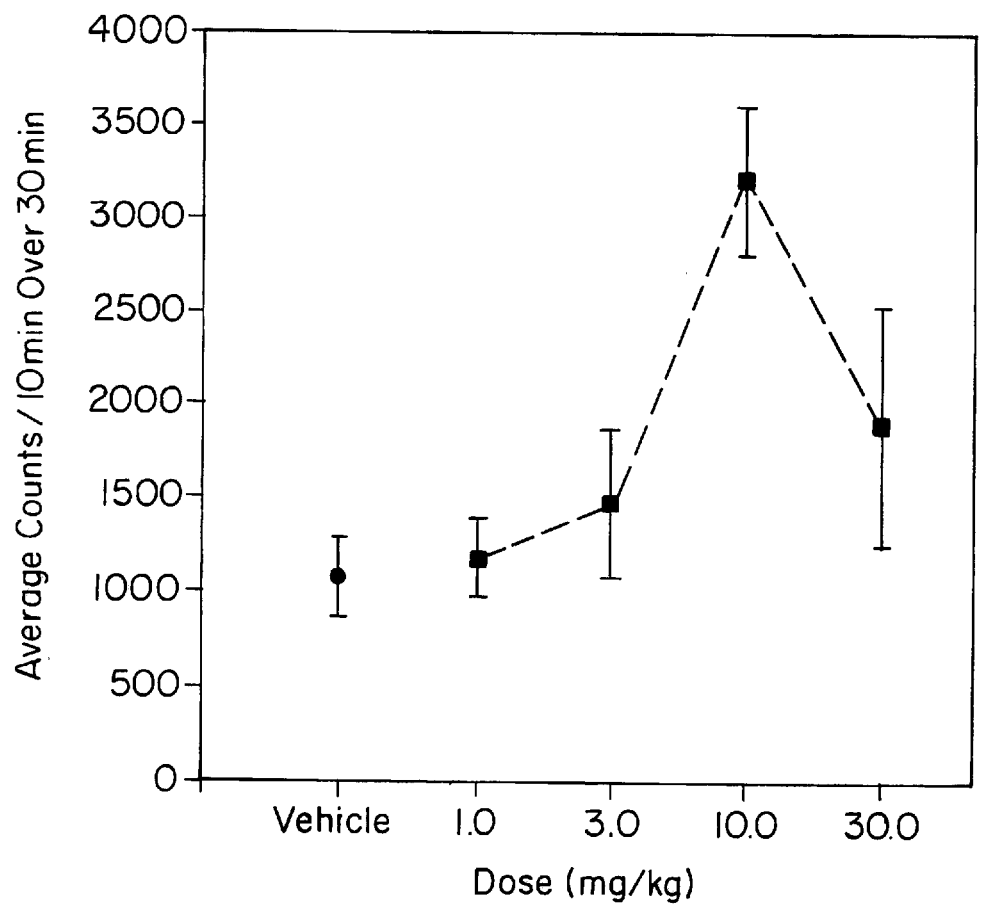
FIG. 6 is a graph showing the average number of ambulation counts/10 minutes over 30 minutes resulting from the stimulation of locomotor activity in mice by Compound 3 versus the dosage of Compound 3 administered to the mice.
Figure 7:
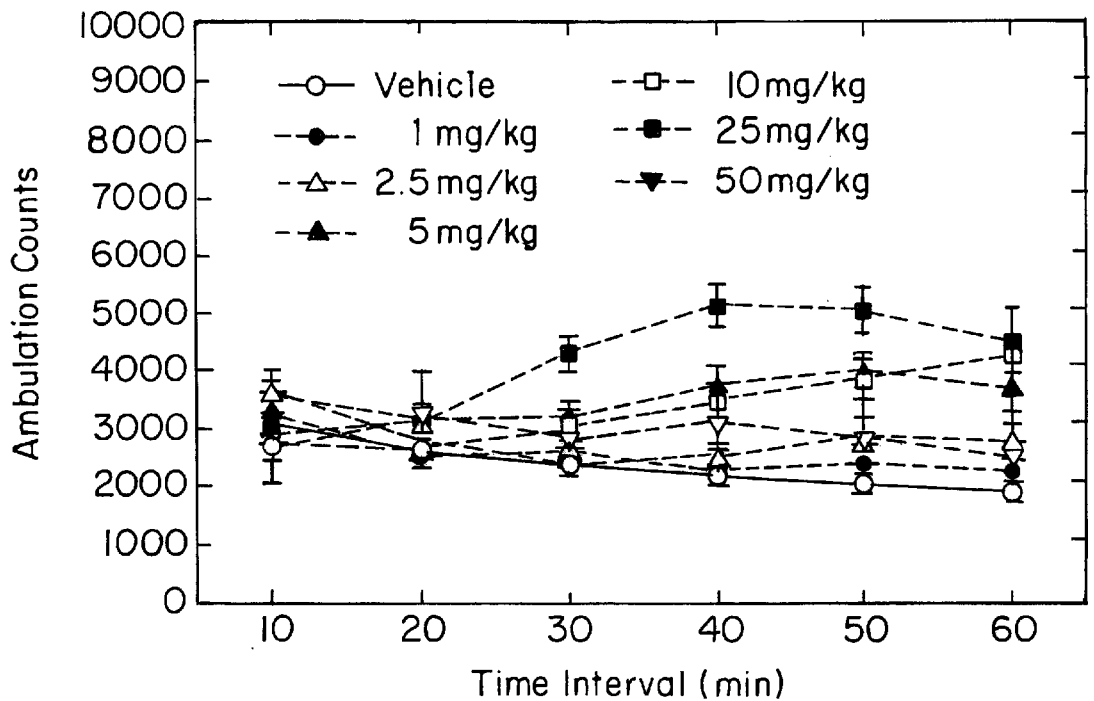
FIG. 7 is a graph showing the number of ambulation counts resulting from the stimulation of locomotor activity in mice over time by the administration of 1) vehicle; 2) 1 mg/kg of Compound 4; 3) 3 mg/kg of Compound 4; 4) 10 mg/kg of Compound 4; and 5) 30 mg/kg of Compound 4.
Figure 8:
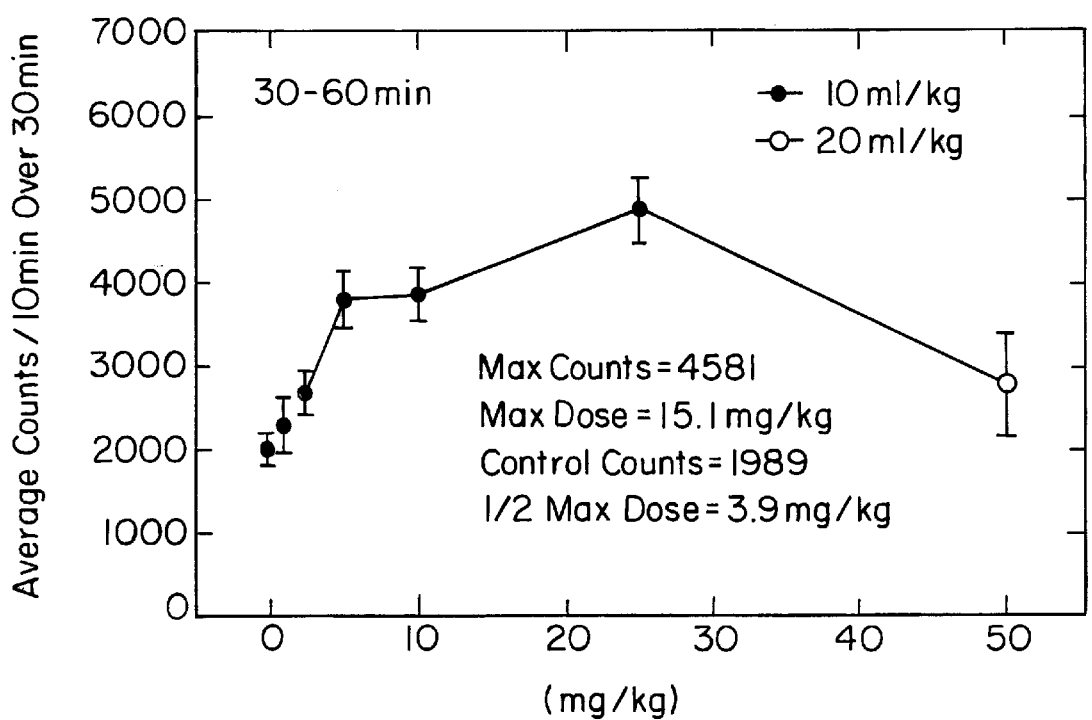
FIG. 8 is a graph showing the average number of ambulation counts/10 minutes over 30 minutes resulting from the stimulation of locomotor activity in mice 4 versus the dosage of Compound 4 administered to the mice.

In a preferred embodiment, the compound of the present invention is represented by Structural Formula (II):

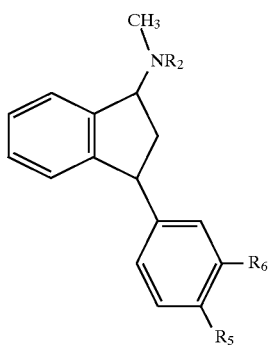

R2 is as described for Structural Formula (I). R5 and R6 are each —H or a substituent, as described for Ring B in Structural Formula (I). More preferably, R2 is n-propyl or tert-butyl. Even more preferably, R5 and R6 are each —Cl.

In another preferred embodiment, the compound of the present invention is represented by Structural Formula (II), wherein R2 is a benzyl or substituted benzyl group. R5 and R6 are each —H or a substituent, as described for Ring B in Structural Formula (I). More preferably, R2 is a benzyl group. Even more preferably, R5 and R6 are each —Cl.

An "aryl group" includes carbocyclic aromatic structures. An "aryl group" can be monocyclic (e.g., phenyl) or polycyclic. A polycyclic aromatic group includes moieties having one or more fused carbocyclic aromatic structures, e.g. naphthyl or anthracyl.

Suitable heteroaryl groups include monocyclic or polycyclic aromatic groups containing one or more heteroatoms such as oxygen, nitrogen or sulfur. Suitable monocyclic heterocyclic groups include imidazolyl, thienyl, pyridyl, furanyl, oxazoyl, pyrollyl, pyrimidinyl, furanyl, pyrazolyl, pyrrolyl, thiazolyl and the like. A polycyclic heteroaryl group includes fused structures such as quinonyl, isoquinonyl, indoyl benzimidazoyl, benzothiazolyl, benzothiophenyl, benzofuranyl and benzopyranyl.

A "lower alkyl group" includes C1 to about C10 straight or branched chain hydrocarbons. The hydrocarbon can be saturated or can have one or more units of unsaturation. Preferred lower alkyl groups are straight chain C1–C3 hydrocarbons. Alternatively, lower alkyl groups preferably include C1 to C4 straight chain and branched hydrocarbons.

Suitable substituents for an aryl, heteroaryl, benzyl or lower alkyl group include substituents which do not signifiantly decrease the affinity of the N,N-dialkyl 3-phenyl-1-indamine for the dopamine transporter or the bioavailability of the N,N-dialkyl 3-phenyl-1-indamine.

Suitable examples include halogens, lower alkyl, hydroxy, (lower alkyl)—O—, (substituted lower alkyl)—O—, —CN, —NO₂, —NH₂ (lower alkyl)NH—, (substituted alkyl)NH—, dialkylamine and (substituted dialkyl)amine.

In the method of treatment disclosed herein the trans stereoisomer of the compound represented by Structural Formula (I) is preferentially administered. Examples of cis and trans stereoisomers are shown below.

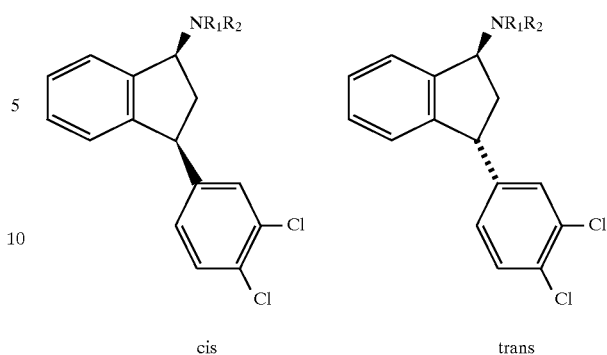

cis                              trans

The compound can be administered as a racemic mixture of enantiomers, as an optically pure enantiomer or as a mixture enriched in one enantiomer.

A "therapeutically effective" amount of a compound is the amount of compound which decreases or alleviates the severity of the symptoms associated with a disease, e.g., Parkinson's disease, attention deficit disorder or cocaine abuse, in an individual being treated with the compound. In the case of treatment of cocaine abuse, a "therapeutically effective" amount of a compound can be the amount of compound which decreases the craving for cocaine of an individual who abuses cocaine. Typically, a "therapeutically effective amount" of the compound ranges from about 1 mg/day to about 1000 mg/day.

The compounds of the present invention can be administered by a variety of known methods, including orally, rectally, or by parenteral routes (e.g., intramuscular, intravenous, subcutaneous, nasal or topical). The form in which the compounds are administered will be determined by the route of administration. Such forms include, but are not limited to capsular and tablet formulations (for oral and rectal administration), liquid formulations (for oral, intravenous, intramuscular or subcutaneous administration) and slow releasing microcarriers (for rectal, intramuscular or intravenous administration). The formulations can also contain a physiologically acceptable vehicle and optional adjuvants, flavorings, colorants and preservatives. Suitable physiologically acceptable vehicles may include saline, sterile water, distilled water, Ringer's solution, and isotonic sodium chloride solutions. The specific dosage level of active ingredient will depend upon a number of factors, including, for example, biological activity of the particular preparation, age, body weight, sex and general health of the individual being treated.

The pharmaceutical compositions used in the methods of treatment disclosed herein can contain one N,N-dialkyl 3--phenyl-1-indamine. Alternatively, the pharmaceutical composition can contain more than one N,N-dialkyl 3-phenyl-1-indamine, e.g. the individual is being administered a mixture of N,N-dialkyl 3-phenyl-1-indamines.

When a mixture is being administered, virtually any ratio of N,N-dialkyl 3-phenyl-1-indamines can be used that is non-toxic and therapeutically effective.

The compounds of the present invention used in the treatment of an individual with Parkinson's disease or attention deficit disorder can be co-administered with other pharmaceutically active agents used in the treatment of Parkinson's disease or attention deficit disorder. The compounds of the present invention used in the treatment of an individual who abuses cocaine can be combined with other therapies used to treat individuals who abuse cocaine. Such therapies can include the co-administration of other pharmaceutically active agents used to treat cocaine abuse or psychological therapies.

When the compounds of the present invention are used in combination with other pharmaceutically active agents, the specific combination will vary, depending on a number of factors, including, for example, activity of the agents, their side-effects, and the weight, age, sex and general health of the individual being treated.

The preparation of compounds of the present invention is shown in the Scheme and described more fully in Example 1. It is noted that compounds represented by Structural Formula (I) in which Ring A is an aryl group other than phenyl can be prepared by using the corresponding aryl aldehyde as a starting material in place of benzaldehyde. For example, compounds represented by Structural Formula (I) in which Ring A is a 1-naphthyl or 1-thiophene group can be prepared by using 1-CHO-napthalene or 1-CHO-thiophene as a starting material in place of benzaldehyde.

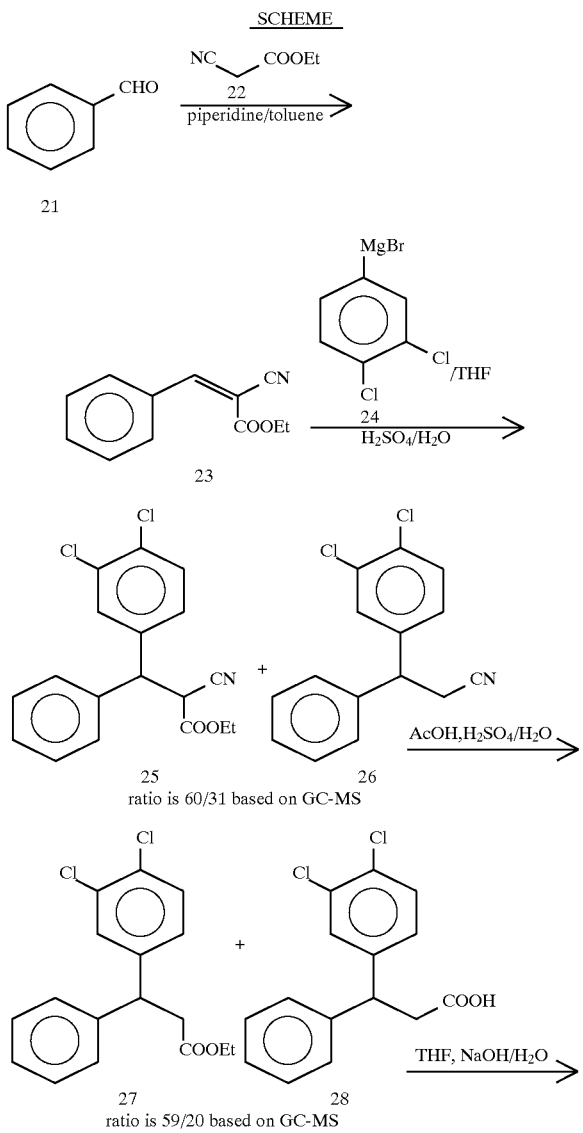

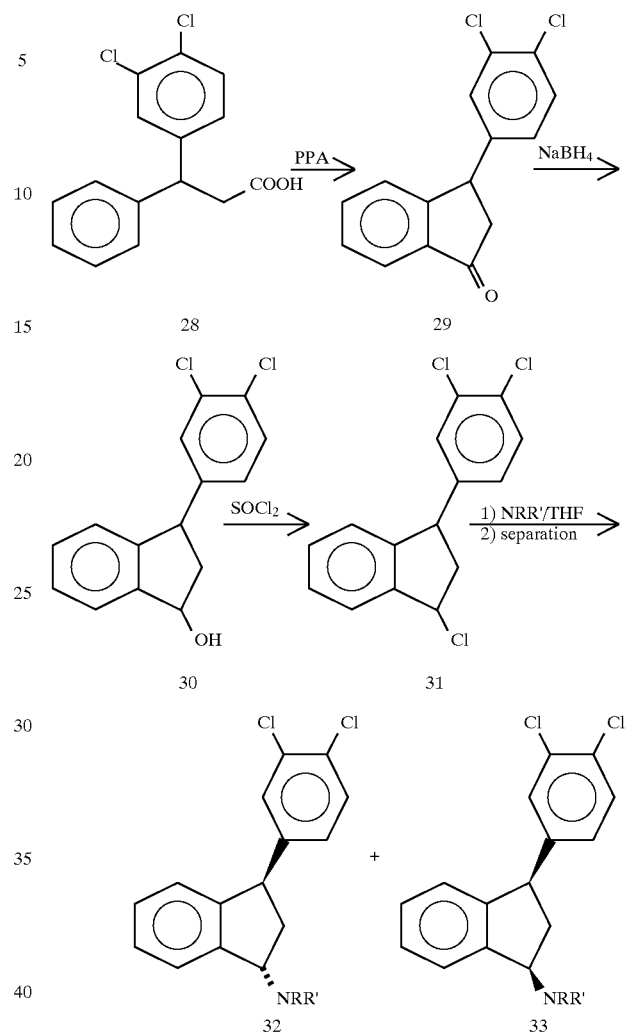

The invention is further illustrated by the following examples.

EXEMPLIFICATION

EXAMPLE 1

Preparation of N,N-Dialkyl 3-Phenyl-1-Indamines
Preparation of Compound 23

A solution of benzaldehyde (318 g) and ethyl cyanoacetate (383 g) in toluene (1.5 L) was brought to boiling in a flask equipped with a Dean-Stark trap. After ~60 mL of water was collected, the resulting mixture was concentrated under reduced pressure. Vacuum drying gave 690 g of a wet solid. Recrystallization from 1.5 L of THF and 3 L of hexanes gave a pale-yellow solid (360 g).
Preparation of Compound 25

Magnesium turnings (6.7 g) were activated by heating with iodine (0.02 g) under an Ar atmosphere. After anhydrous THF (200 mL) was added, a solution of 1-bromo-3, 4-dichlorobenzene (63.1 g) in anhydrous THF (100 mL) was added under Ar slowly so that gentle boiling was maintained. The resulting mixture was then brought to reflux for 0.5 hours. The resulting mixture was cooled to room-temperature and slowly added to a solution of 23 in anhydrous THF (100 mL) under Ar via cannula. The stirring was continued for 1 hour. The resulting mixture was poured onto a mixture of ice (200 g) and concentrated $H_2SO_4$ (10 mL). The organic layer was separated from the aqueous layer and the aqueous layer was extracted with EtOAc (2×100 mL). The combined EtOAc solution was washed with water (200 mL) and then with brine (200 mL). Solvent evaporation under reduced pressure followed by vacuum drying gave a thick orange oil (96.7 g).

Preparation of Compound 28

A mixture of crude 25 (96 g), AcOH (192 mL), $H_2SO_4$ (96 mL), and water (96 mL) was brought to reflux (20 hours). The resulting mixture was poured onto ice (200 g). The organic layer was separated from the aqueous layer and the aqueous layer was extracted with $CH_2Cl_2$ (200 mL). The combined organic solution was washed with water (200 mL) and then with brine (200 mL). Solvent evaporation under reduced pressure followed by vacuum drying gave a thick brown oil (87.4 g). THF (87 mL), NaOH (17.5 g) and water (87 mL) were added to the thick oil. The resulting mixture was brought to reflux for 2.5 hours. Water (87 mL) was added and the mixture was acidified with 37% HCl(aq) (50 mL, pH≦1). The organic layer was separated from the aqueous layer and the aqueous layer was extracted with EtOAc (87 mL). The combined organic solution was washed with water (200 mL) and then with brine (200 mL). Solvent evaporation under reduced pressure and vacuum drying provided a thick brown syrup (78.6 g).

Preparation of Compound 29

A mixture of the crude acid 28 (78.6 g) and polyphosphoric acid (225 g) was stirred under an Ar atmosphere for 3 hours at ~100° C. The resulting mixture was poured onto ice (225 g) and EtOAc (225 mL). The organic layer was separated from the aqueous layer and the aqueous layer was extracted with EtOAc (2×110 mL). The combined EtOAc solution was washed with water (110 mL) and brine (110 mL). Solvent evaporation under reduced pressure and vacuum drying gave a wet brown solid. A solution of the solid in $CH_2Cl_2$ was passed through a silica gel plug (9 in I.D., 3 in high) with $CH_2Cl_2$. Solvent evaporation of the collected fractions under reduced pressure followed by vacuum drying finishing with a wet brown solid (57.4 g).

Preparation of Compound 30

$NaBH_4$ (2.46 g) was added in three portions to a mixture of ketone 29 (56.6 g), EtOAc (260 mL), and EtOH (120 mL) with stirring under an Ar atmosphere. After 0.5 h, more $NaBH_4$ (0.5 g) was added and the stirring was continued for another 0.5 hours. Solvent evaporation under reduced pressure gave a thick dark brown oil. Water (260 mL) was added and the mixture was extracted with EtOAc (260 mL and then 2×80 mL). The combined organic solution was washed with brine and water. Solvent evaporation under reduced pressure gave a brown syrup, which was passed through a silica gel plug (9 in I.D., 3.5 in high) with 800 mL of 80% $CH_2Cl_2$/hexanes, followed by 500 mL of $CH_2Cl_2$, and then with 500 mL of 20% $EtOAc/CH_2Cl_2$. The fractions containing the desired alcohols were collected. Solvent evaporation under reduced pressure and vacuum drying gave a brown residue (46.8 g).

Preparation Compound 31

$SOCl_2$ was slowly added with stirring to a solution of alcohol 30 (22.5 g) in anhydrous toluene (135 mL) under an Ar atmosphere. The stirring was continued for 2 hours. Water (135 mL) was added. The organic solution was washed with water (135 mL) and then with brine (70 mL). Solvent evaporation under reduced pressure and vacuum drying afforded a thick brown oil (13.7 g).

Preparation of Compounds 32 and 33

A mixture of chlorides 31 (48.9 g) and excess amine (dimethylamine, 61.9 g; typically, 6–9 equivalents) in anhydrous THF (260 mL) was heated in a bomb to 100°–130° C. for 20 hours with stirring. The resulting material was cooled to <300° C. Saturated $Na_2CO_3$(aq) (400mL) was added and the organic layer was separated from the aqueous layer. The aqueous layer was extracted with EtOAc (150 mL). The combined organic solution was washed with brine (200 mL). Solvent evaporation under reduce pressure and vacuum drying gave a thick black oil (48.1 g). The resulting crude product was subjected to purification either by preparative TLC, chromatography, or HPLC with a partial purification either by a silica gel plug or salt formation beforehand. For the N,N-dimethylindanamines, the purification was done as described below. The HCl salt formation from the black oil in a mixture of EtOH, ether, and acetone gave an almond solid enriched with the cis-isomer. The freebase enriched with the trans-isomer were recovered by treatment with saturated $Na_2CO_3$(aq). Maleic acid salt formation from the freebases using EtOAc, EtOH, acetones, hexanes and ether gave a maleic acid salt as a greenish almond solid. Freebase from the mother liquor was again recovered by treatment with saturated $Na_2CO_3$(aq). The recovered freebase was partially purified by passing through a silica gel plug. The recovered freebase, the freebase from the HCl salt, and the freebase from the maleic acid salt were subjected to HPLC separation (Phenomenex Primesphere $5\mu$ silica 110 column, 250×21.2 mm; UV, 268 nm; 0.05% $Et_2NH/EtOAc$, 10 mL/min; cis-isomer, 17 minutes; trans-isomer, 20 minutes) to give pure 32 and 33.

Salt Formation of Compound 32 and 33

Freebases 32 and 33 were converted the their corresponding HCl, maleic acid or oxalic acid salts. A typical HCl salt formation involved dissolving a freebase in ether, adding 1.1 equivalents of 1M HCl/ether with stirring, vacuum filtration of the resulting suspension, washing the solid with ether and vacuum drying at an appropriate elevated temperature. A typical maleic or oxalic acid salt formation involved dissolving a freebase in ErOH and ether, adding a solution of maleic or oxalic acid (1.05 mol equivalents) in EtOH with stirring, adding more ether to the resulting mixture, vacuum filtration, washing the solid with ether, and vacuum drying at an appropriate elevated temperature.

Compounds 2–7 were prepared as described above, except that dimethylamine was replaced with the appropriate amine in the reaction with chlorides 31. In addition, the corresponding N-methyl-N-iso-propyl (Compound 8), N-(n-propyl) (Compound 9) and N-methyl-N-benzyl (Compound 10) phenylindamines were prepared by replacing dimethylamine with methyl(2-propyl)amine, n-propylamine or methyl(benzyl)amine, respectively, in the reaction with chlorides 31.

The chemical shifts observed in the $^{13}C$ NMR spectrum of the maleic acid salt of Compound 1 in DMSO-$d_6$ are as follows: 36.6, 40.4, 42.1, 70.5, 127.1, 128.4, 129.6, 130.0, 131.1, 131.7, 132.3, 132.6, 133.0, 137.5, 137.6, 146.9, 149.7, 169.1.

The chemical shifts observed in the $^{13}C$ NMR spectrum of the HCl salt of Compound 2 in DMSO-$d_6$ are as follows: 33.9, 34.1, 35.1, 36.6, 47.8, 48.0, 54.1, 56.7, 66.5, 68.4, 125.1, 125.3, 127.4, 127.5, 127.7, 128.2, 128.6, 128.62, 129.2, 129.27, 129.3, 129.9, 130.0, 130.26, 130.3, 130.5, 130.7, 130.8, 131.1, 131.2, 131.5, 135.4, 135.7, 145.3, 147.9, 148.5.

The chemical shifts observed in the $^{13}C$ NMR spectrum of the oxalic acid salt of Compound 3 in DMSO-$d_6$ are as follows: 11.6, 36.3, 36.7, 49.5, 49.7, 69.1, 127.0, 128.4, 129.5, 130.0, 131.0, 131.6, 132.0, 132.6, 132.9, 138.2, 147.4, 149.6, 166.5.

The chemical shifts observed in the $^{13}$C NMR spectrum of the HCl salt of Compound 4 in DMSO-d$_6$ are as follows: 12.9, 39.4, 41.6, 49.2, 61.9, 126.5, 128.4, 129.1, 130.0, 131.0, 131.5, 131.7, 132.6, 133.0, 139.4, 146.6, 138.9.

The chemical shifts observed in the $^{13}$C NMR spectrum of the HCl salt of Compound 5 in DMSO-d$_6$ are as follows: 31.7, 39.1, 49.1, 63.1, 126.9, 128.1, 129.2, 130.0, 131.0, 131.5, 131.8, 132.6, 133.0, 139.3, 146.9, 148.8.

The chemical shifts observed in the $^{13}$C NMR spectrum of the HCl salt of Compound 6 in DMSO-d$_6$ are as follows: 25.6, 40.3, 47.9, 56.7, 57.8, 124.7, 126.8, 127.2, 128.2, 129.2, 129.7, 129.8, 130.8, 131.1138.5, 145.0, 147.0.

The chemical shifts observed in the $^{13}$C NMR spectrum of the HCl salt of Compound 7 in CDCl$_3$ are as follows: 25.3, 26.1, 29.4, 34.8, 37.0, 43.8, 48.7, 49.3, 64.4, 64.8, 65.7, 125.2, 126.4, 126.9, 127.1, 127.6, 128.1, 128.8, 129.2, 129.7, 130.0, 130.7, 130.87, 130.9, 131.0, 131.2, 132.7, 132.9, 135.8, 136.2, 143.0, 144.2, 145.2, 149.4.

The chemical shifts observed in the $^{13}$C NMR spectrum of the HCl salt of Compound 8 in DMSO-d$_6$ are as follows: 16.1, 17.3, 18.1, 18.6, 31.7, 32.1, 33.7, 37.7, 47.6, 47.9, 54.6, 56.1, 65.1, 65.8, 125.2, 127.2, 127.3, 127.5, 127.7, 128.2, 128.4, 129.2, 129.3, 129.8, 130.0, 130.2, 130.4, 130.76, 130.8, 131.1, 135.5, 136.5, 145.0, 145.4, 147.76, 148.9.

The chemical shifts observed in the $^{13}$C NMR spectrum of the HCl salt of Compound 9 in DMSO-d$_6$ are as follows: 11.0, 19.1, 37.6, 46.0, 47.4, 60.4, 125.0, 126.6, 127.3, 128.2, 129.2, 129.7, 129.9, 130.7, 131.1, 137.5, 145.1, 147.1.

The chemical shifts observed in the $^{13}$C NMR spectrum of the HCl salt of Compound 10 in DMSO-d$_6$ are as follows: 33.9, 34.1, 35.1, 36.6, 47.8, 48.0, 54.1, 56.7, 66.4, 68.4, 125.1, 125.3, 127.4, 127.5, 127.7, 128.2, 128.3, 128.60, 128.62, 129.2, 129.27, 129.3, 129.88, 129.9, 130.0, 130.3, 130.4, 130.5, 130.7, 130.8, 131.1, 131.2, 131.5, 135.4, 135.7, 135.3, 135.4, 147.9, 148.5.

EXAMPLE 2

A dose response study of induced locomotor stimulation was conducted according to the following procedure. The study was conducted using a 16 or 32 Digiscan locomotor activity testing chambers (40.5×40.5×30.5 cm) housed in sets of two, within sound-attenuating chambers. A panel of infrared beams (16 beams) and corresponding photodetectors were located in the horizontal direction along the sides of each activity chamber. A 15-W incandescent light above each chamber provided dim illumination. Fans provided an 80-dB ambient noise level within the chamber. Separate groups of 8 non-habituated male Swiss-Webster mice (Hsd:ND4, aged 2–3 months) were injected via the intraperitoneal (IP) route with either vehicle (deionized water for Compounds 1–4, carboxymethylcellulose for Compound 6 or methyl cellulose for Compound 7)) or test compound (1, 2.5, 5, 10, 25 or 50 mg/kg for Compound 3; 1, 3, 10 and 30 mg/kg for Compounds 1, 2 and 4; 3, 10, 30 or 100 mg/kg for Compound 6; and 1, 3, 10, 30 and 10 mg/kg for Compound 7). Compounds 1–4 were injected immediately prior to locomotor activity testing. Compound 5 and 6 were injected 20 minutes prior to locomotor activity testing. In all studies, horizontal activity (interruption of photocell beams) was measured for 1 hour within 10 minute periods. Testing was conducted with one mouse per activity chamber.

Figure 11:
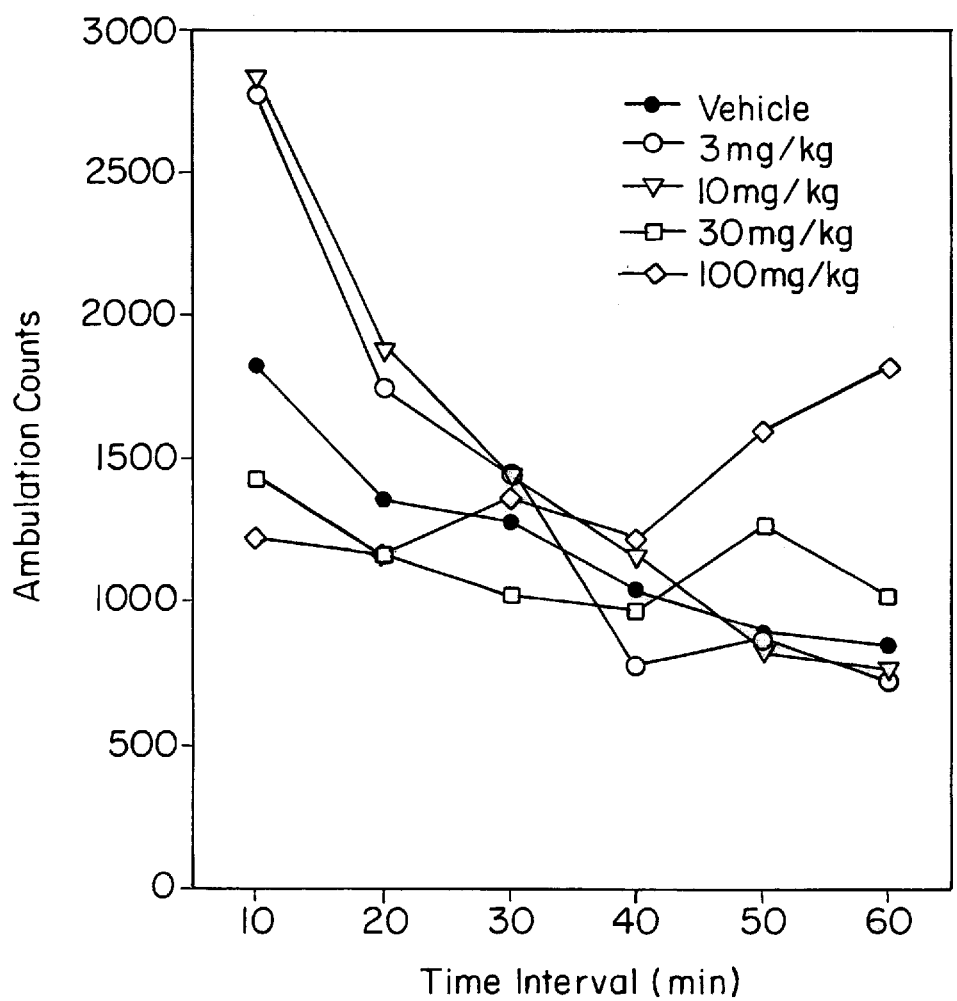
FIG. 11 is a graph showing the number of ambulation counts resulting from the stimulation of locomotor activity in mice over time by the administration of 1) vehicle; 2) 3 mg/kg of Compound 6; 3) 10 mg/kg of Compound 6; 4) 30 mg/kg of Compound 6 and 5) 100 mg/kg of Compound 6.
Figure 12:
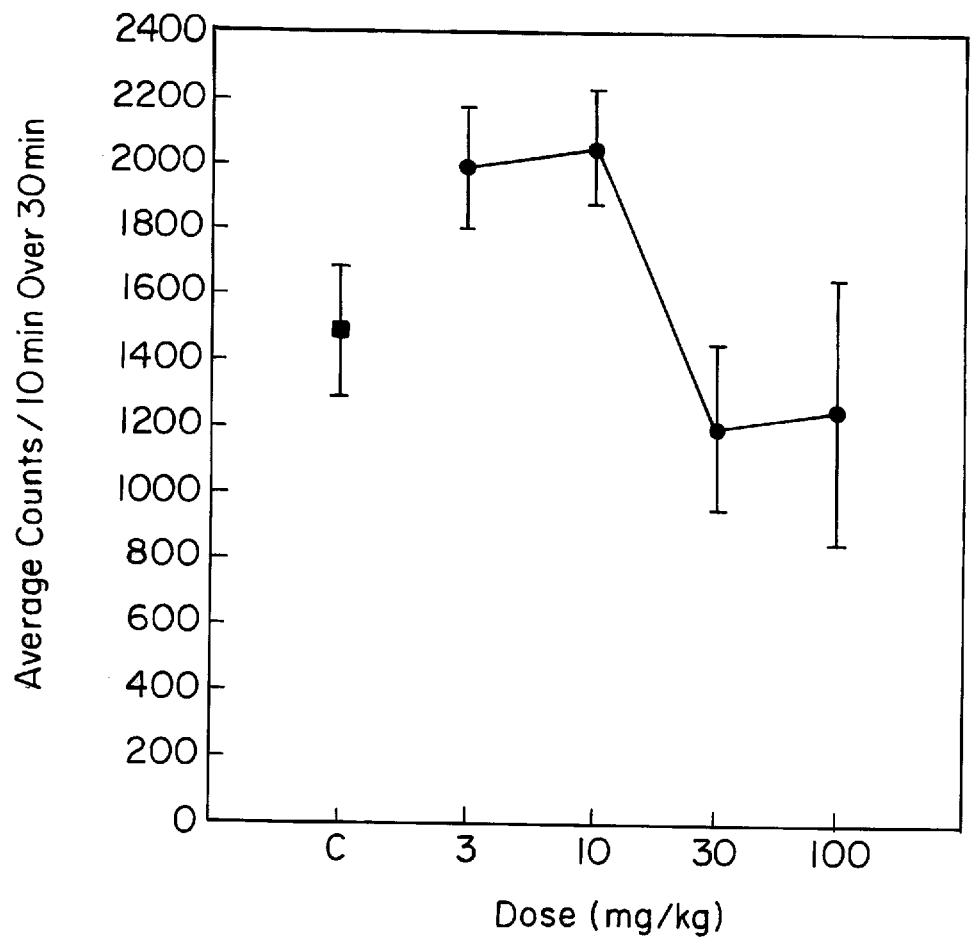
FIG. 12 is a graph showing the average number of ambulation counts/10 minutes over 30 minutes resulting from the stimulation of locomotor activity in mice versus the dosage of Compound 6 administered to the mice.
Figure 13:
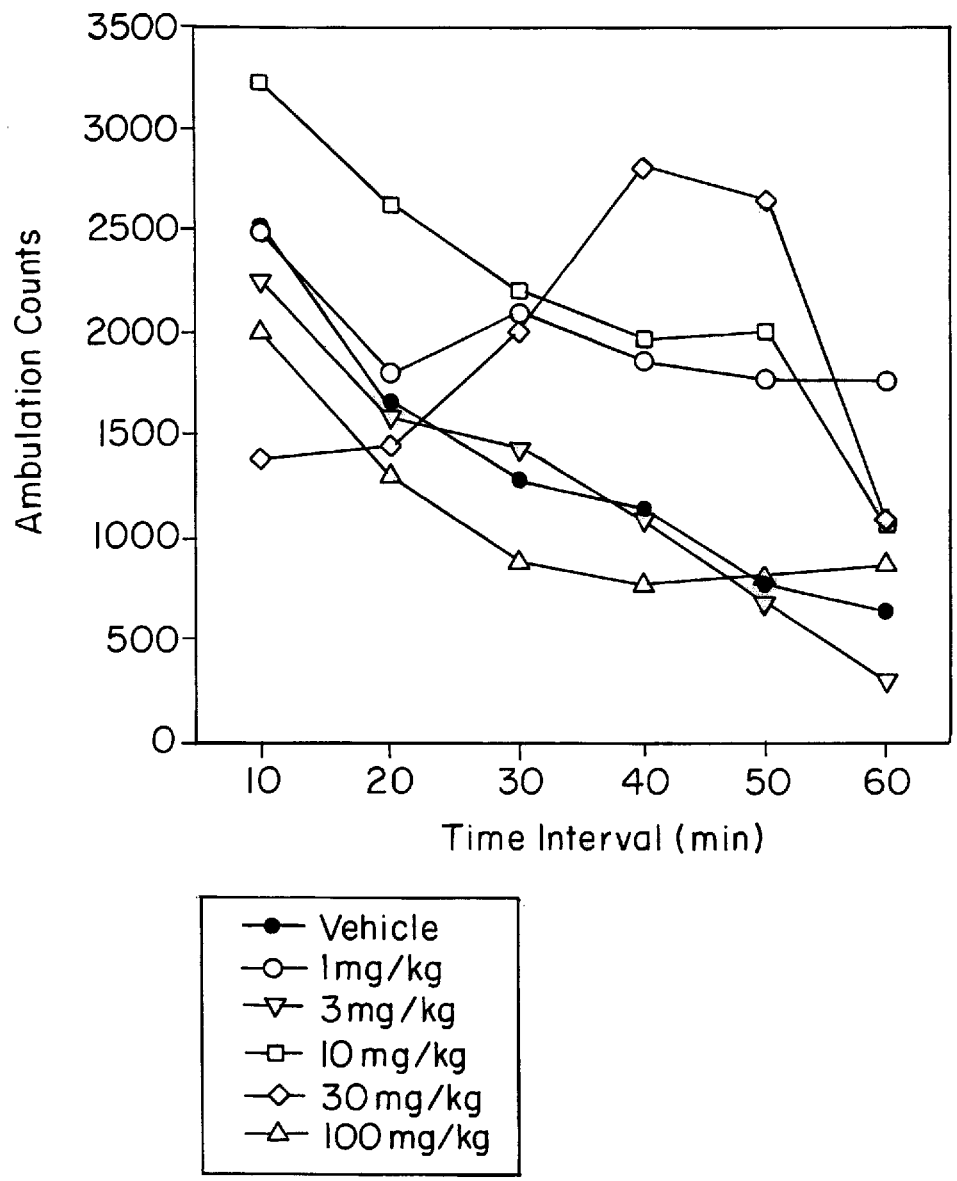
FIG. 13 is a graph showing the number of ambulation counts resulting from the stimulation of locomotor activity in mice over time by the administration of 1) vehicle; 2) 1 mg/kg of Compound 7; 3) 3 mg/kg of Compound 7; 4) 10 mg/kg of Compound 7; 5) 30 mg/kg of Compound 7 and 100 mg/kg of Compound 7.
Figure 14:
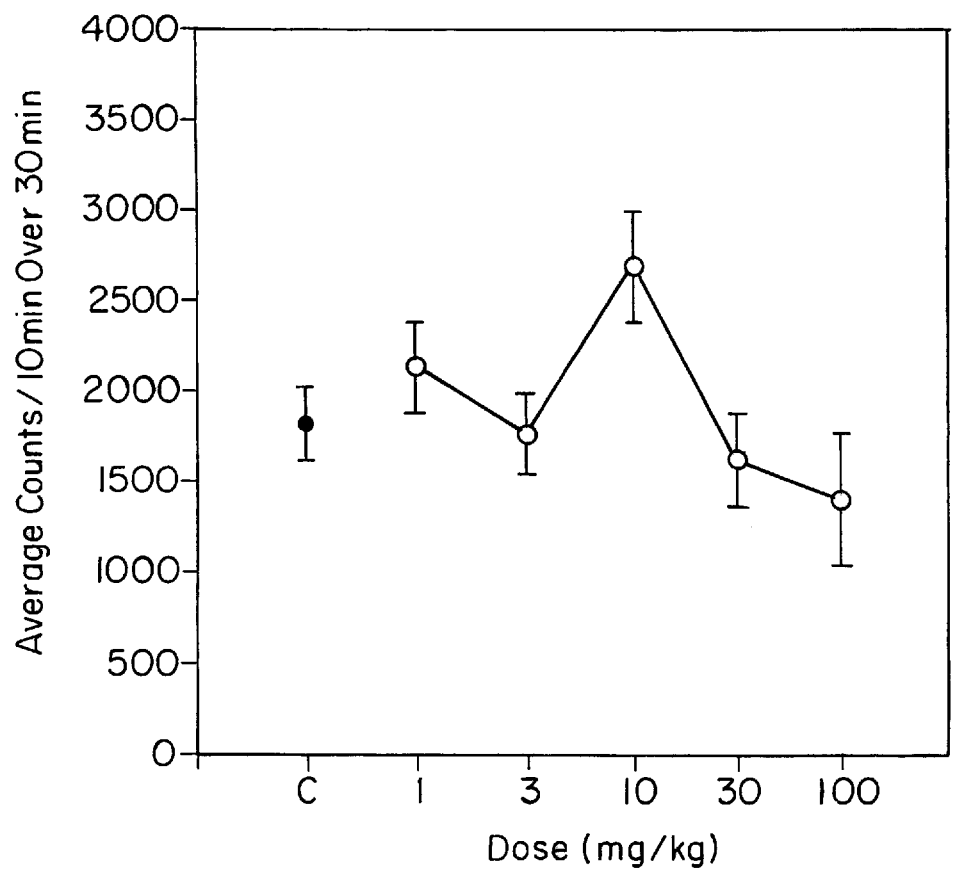
FIG. 14 is a graph showing the average number of ambulation counts/10 minutes over 30 minutes resulting from the stimulation of locomotor activity in mice versus the dosage of Compound 7 administered to the mice.

FIGS. 1, 3, 5 and 7 show average horizontal activity counts/10 minutes as a function of time, immediately following injection of Compound 1, Compound 2, Compound 3 and Compound 4, respectively. FIGS. 11 and 13 show average horizontal activity counts/10 minutes as a function of time, beginning twenty minutes following injection of Compound 6 and Compound 7, respectively. The period 30–60 minutes was selected for analysis of dose-response data. Using TableCurve 2D v2.03 software (Jandel Scientific), the mean average horizontal activity counts/10 minutes for this period were fit to a 3-parameter logistic peak function of $\log_{10}$ dose (with the constant set to 1989, the mean of the vehicle-treated group), and the maximum effect estimated from the resulting curve. The ED$_{50}$ for Compound 1–6 (dose producing ½ maximal stimulant activity) was estimated from a linear regression against $\log_{10}$ dose of the ascending portion of the dose-effect curve is shown in Table I below. Compound 7 inhibited locomotor activity; the dose producing ½ maximal inhibitory activity ID$_{50}$ was 184 mg/kg. FIGS. 2, 4, 6, 8, 12 and 14 show average horizontal activity counts/10 minutes over 30 minutes versus the amount administered of Compound 1, Compound 2, Compound 3, Compound 4, Compound 6 and Compound 7, respectively.

TABLE I

Locomotor Activity in the Rat
ED$_{50}$ of Synthesized Compounds AD$_{50}$; of Synthesized
Compounds Against 20 mg/kg of Cocaine

| Compound | ED$_{50}$ (mg/kg) | Maximal Effect Relative to Cocaine | AD$_{50}$ (mg/kg) |
|---|---|---|---|
| 4 | 3.90 | 1.07 | not tested |
| 1 | 4.88 | 0.82 | not tested |
| 2 | 5.65 | 0.51 | 13.76 |
| 3 | 10.8 | 0.93 | Not tested |
| 6 | 505.7 | — | 23.6 |

EXAMPLE 3

Compounds 2, 6 and 7 Block the Effects of Cocaine in Mice

This interaction study was conducted using 16 Digiscan locomotor activity testing chambers as described in Example 2. Immediately following IP vehicle or Compound 2 injections (1, 3, 10 or 30 mg/kg) groups of 8 non-habituated male Swiss-Webster mice were injected with either vehicle or 20 mg/kg cocaine IP and immediately placed in the Digiscan apparatus for a one hour session. When testing the effects of Compounds 6 and 7, mice were placed in the Digiscan apparatus twenty minutes after the injection of the test compound or vehicle.

Figure 9:
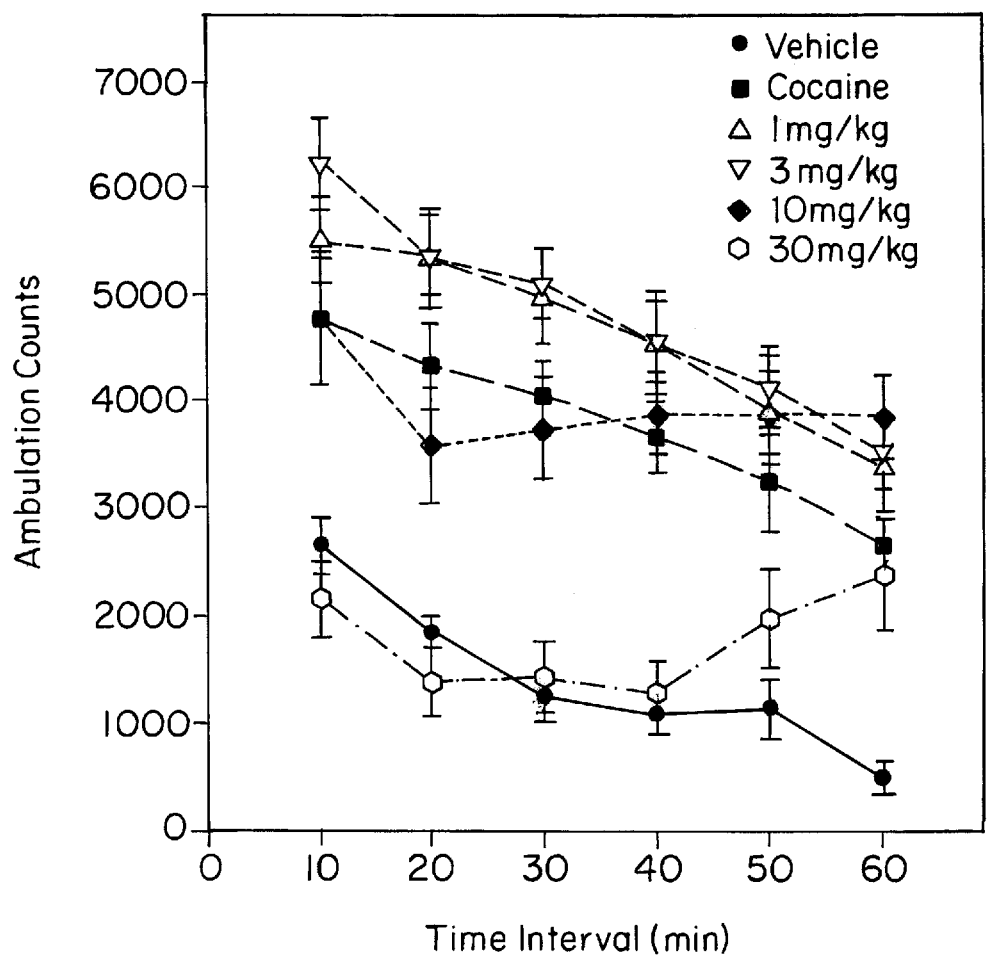
FIG. 9 is a graph showing the number of ambulation counts resulting from the stimulation of locomotor activity in mice over time by the administration of 1) vehicle; 2) cocaine; 3) cocaine and 1 mg/kg of Compound 2; 4) cocaine 3 mg/kg of Compound 2; 5) cocaine and 10 mg/kg of Compound 2; and 6) cocaine and 30 mg/kg of Compound 2.
Figure 10:
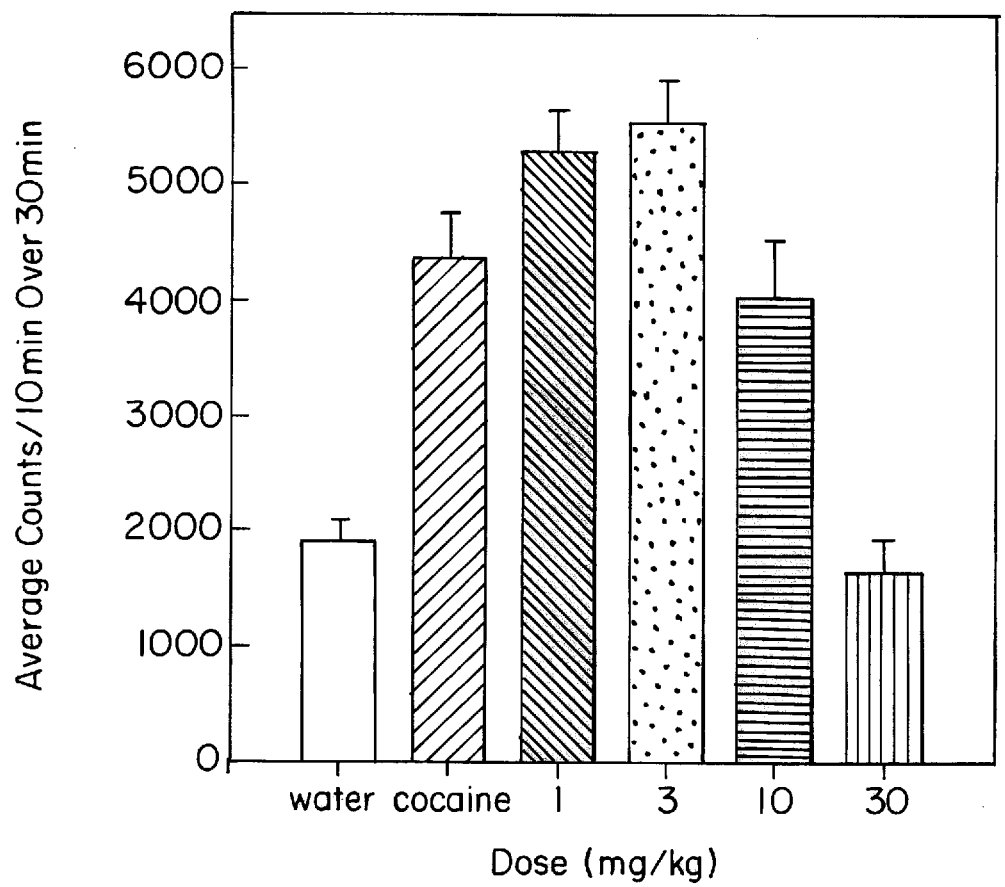
FIG. 10 is a graph showing the average number of ambulation counts/10 minutes over 30 minutes over thirty minutes resulting from the stimulation of locomotor activity in mice induced by the administration of 1) vehicle; 2) cocaine; 3) cocaine and 1 mg/kg of Compound 2; 4) cocaine 3 and mg/kg of Compound 2; 5) cocaine and 10 mg/kg of Compound 2; and 6) cocaine and 30 mg/kg of Compound 2.
Figure 15:
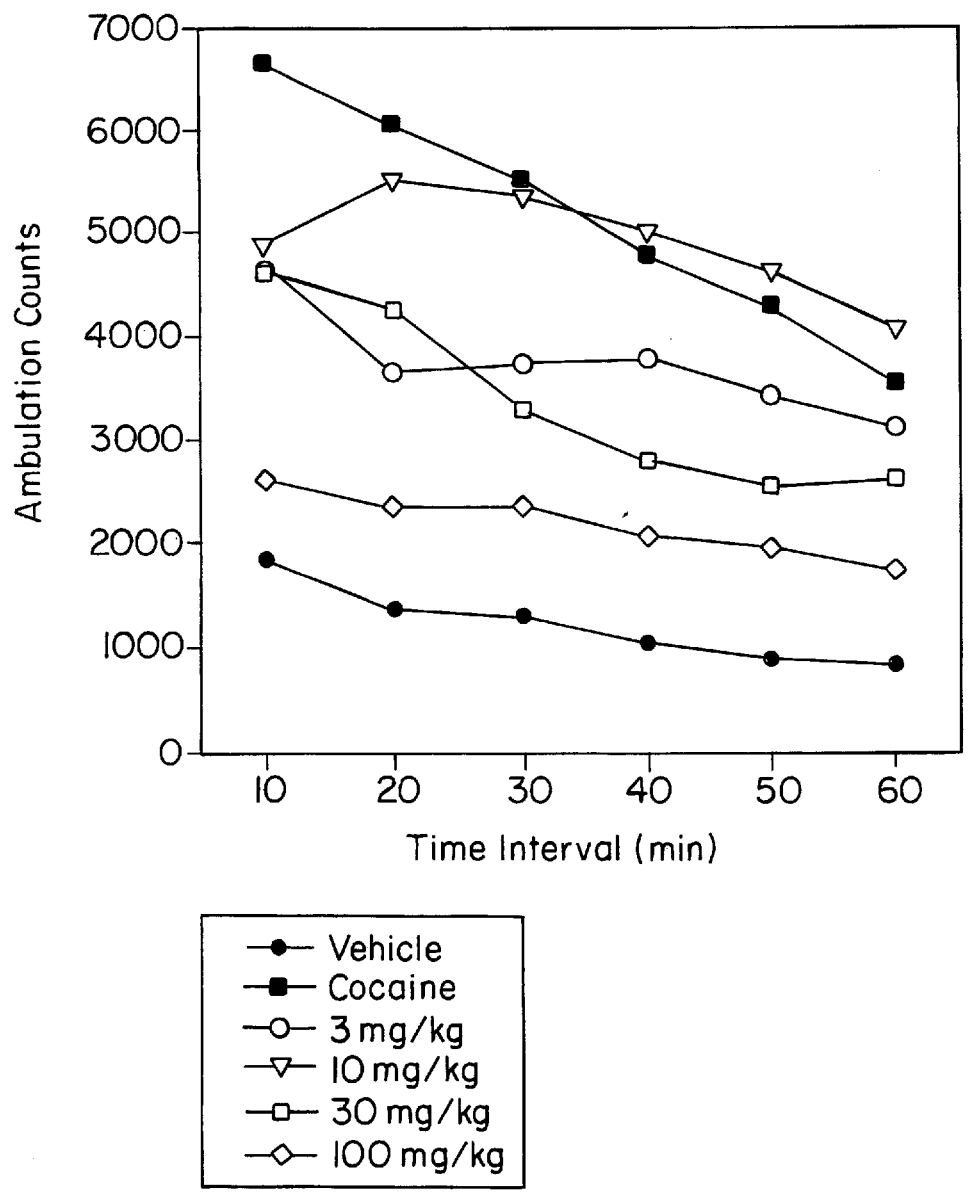
FIG. 15 is a graph showing the number of ambulation counts resulting from the stimulation of locomotor activity in mice over time by the administration of 1) vehicle; 2) cocaine; 3) cocaine and 3 mg/kg of Compound 6; 4) cocaine 10 mg/kg of Compound 6; 5) cocaine and 30 mg/kg of Compound 6; and 6) cocaine and 100 mg/kg of Compound 6.
Figure 16:
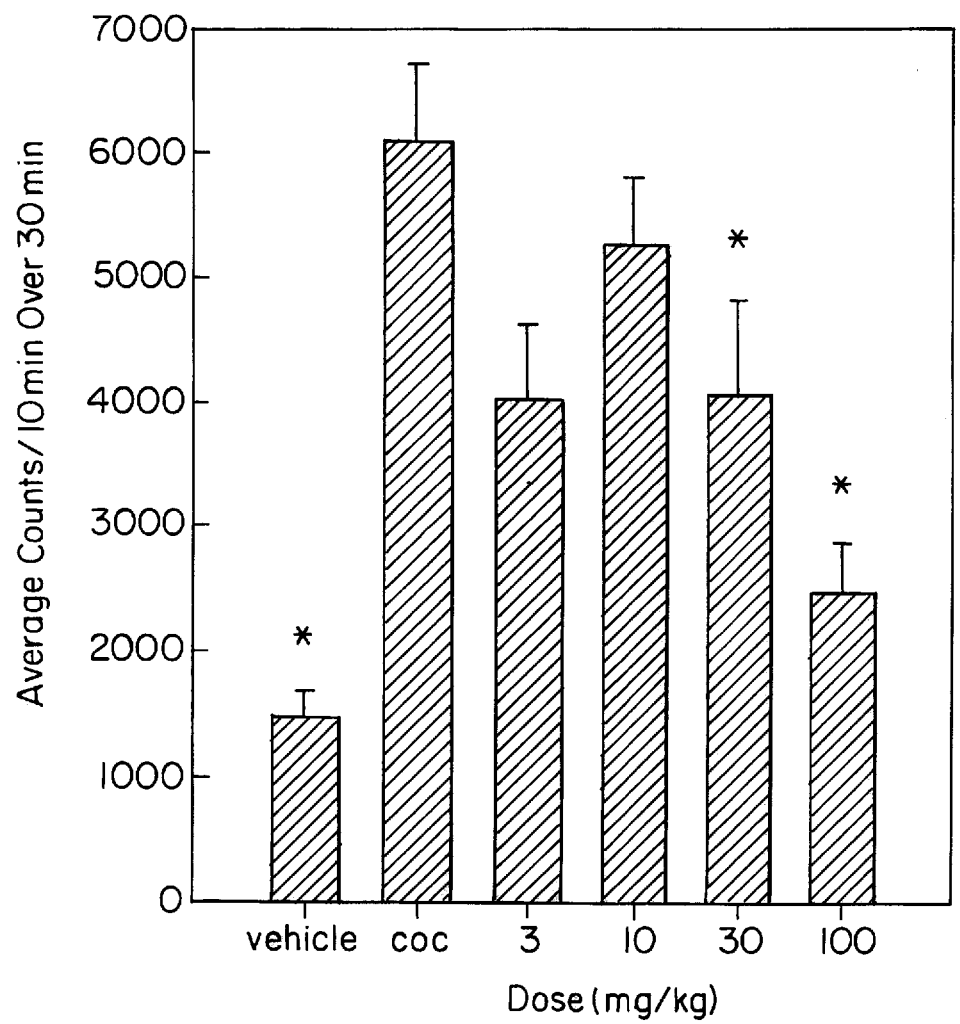
FIG. 16 is a graph showing the average number of ambulation counts/10 minutes over 30 minutes over thirty minutes resulting from the stimulation of locomotor activity in mice induced by the administration of 1) vehicle; 2) cocaine; 3) cocaine and 3 mg/kg of Compound 6; 4) cocaine and 10 mg/kg of Compound 6; 5) cocaine and 30 mg/kg of Compound 6; and 6) cocaine and 100 mg/kg of Compound 6.
Figure 17:
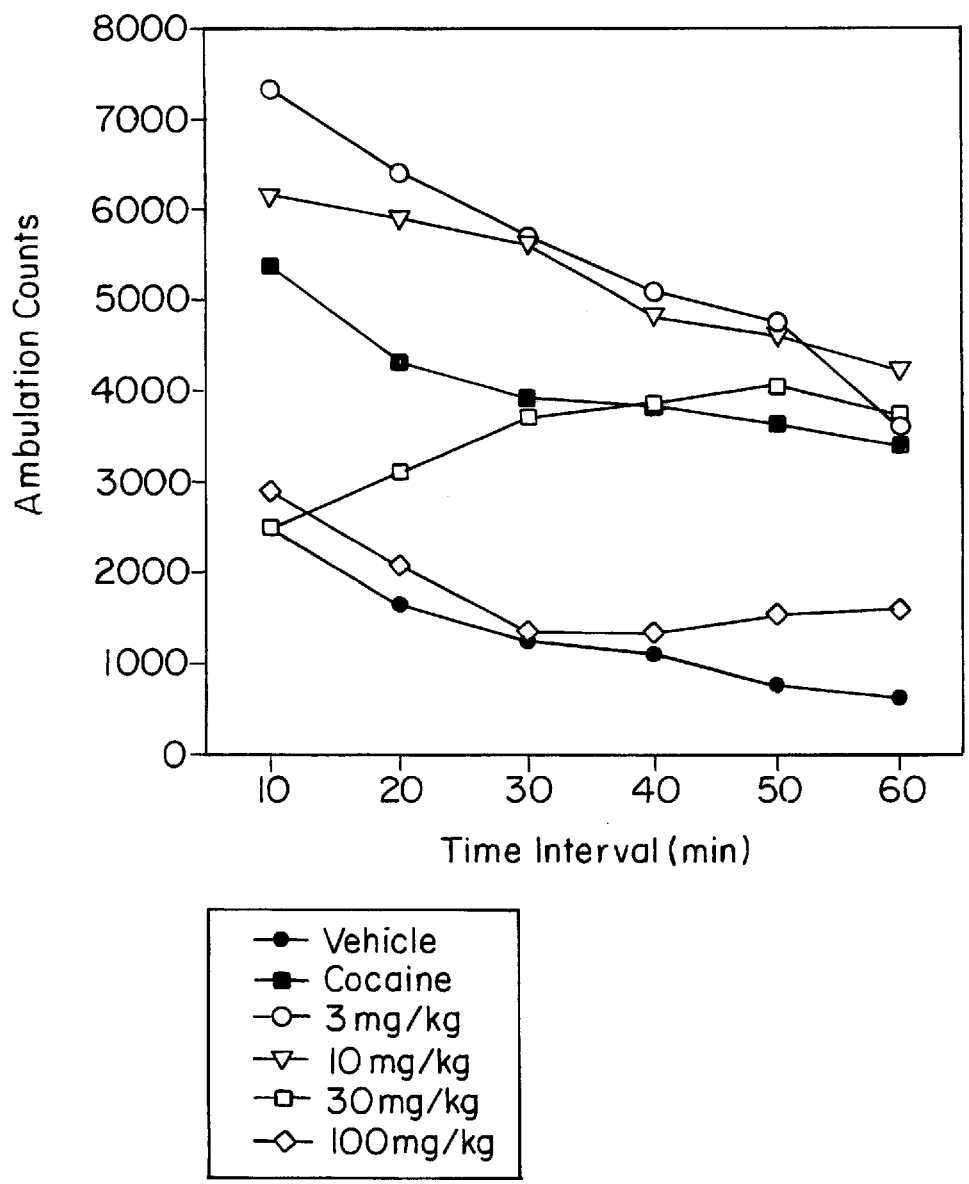
FIG. 17 is a graph showing the number of ambulation counts resulting from the stimulation of locomotor activity in mice over time by the administration of 1) vehicle; 2) cocaine; 3) cocaine and 3 mg/kg of Compound 7; 4) cocaine 10 mg/kg of Compound 7; 5) cocaine and 30 mg/kg of Compound 7; and 6) cocaine and 100 mg/kg of Compound 7.
Figure 18:
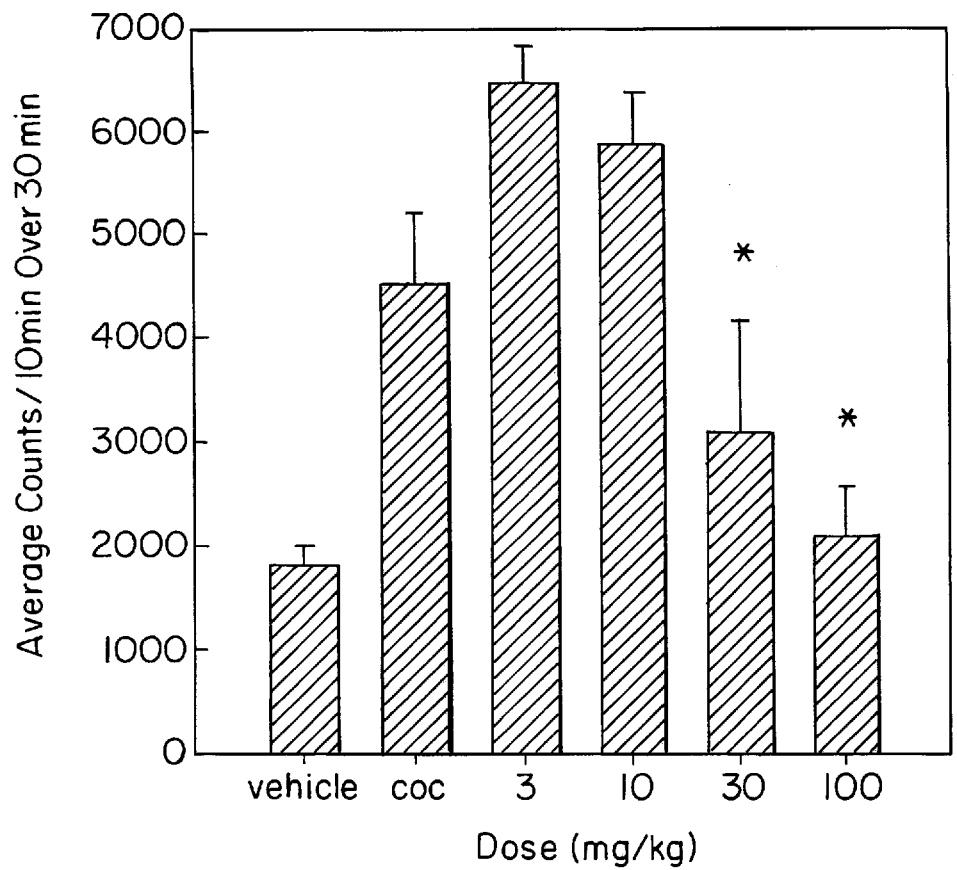
FIG. 18 is a graph showing the average number of ambulation counts/10 minutes over 30 minutes over thirty minutes resulting from the stimulation of locomotor activity in mice induced by the administration of 1) vehicle; 2) cocaine; 3) cocaine and 3 mg/kg of Compound 7; 4) cocaine and 10 mg/kg of Compound 7; 5) cocaine and 30 mg/kg of Compound 7; and 6) cocaine and 100 mg/kg of Compound 7.

FIGS. 9, 15 and 17 show average horizontal activity counts for the different treatment groups as a function of time. The period of 0–30 minutes was selected for analysis of dose-response data because this is the time period in which cocaine produces maximal effects. FIGS. 10, 16 and 18 show average horizontal activity counts/10 min for different treatment groups as a function of dose. In FIG. 10, the bar above "water" represents the effect of vehicle immediately following saline injection; the bar above "cocaine" represents the effect of the 20 mg/kg cocaine immediately following the vehicle injection; The bars above "1", "3", "10" and "30" represent the effects of Compound 2 at the designated doses following the cocaine injection. In FIGS. 16 and 18, the bar above "vehicle" represents the effect of vehicle twenty minutes prior to saline injection; the bar above "coc" represents the effect: of vehicle twenty minutes prior to 20 mg/kg cocaine injection; and the bars above "1", "3", "10", "30" and "100" represent the effects of Compound 6 or Compound 7 at the designated doses twenty minutes prior to 20 mg/kg cocaine injection.

Compounds 2, 6 and 7 antagonized the stimulant effect of cocaine and the AD50 (dose attenuating cocaine-induced stimulation by 50%) was calculated to be 13.76 mg/kg for Compound 2 (3–30 mg/kg Compound 2), 23.6 6 mg/kg Compound 6 (3–100 mg/kg dose range) and 42.5 mg/kg for Compound 7 (3–100 mg/kg dose range). The ordinate value for the $AD_{50}$ was calculated using the mean of the vehicle plus 20 mg/kg cocaine (cocaine) group as the maximum value.

A one-way analysis of variance conducted on $log_{10}$ horizontal activity counts for the selected time period indicated a significant overall effect for the treatment groups; $F(4,35)$ =15.92, p>0.05 for Compound 2; $F(5,42)=7.95$ p<0.5 for Compound 6; and $F((5,42)=8.96$ p<0.5). Planned comparisons (a priori contrast) against the cocaine group showed significant differences for vehicle and 30 mg/kg Compound 2; and for vehicle and 30 and 100 mg/kg Compound 6 and Compound 7. All ps<0.05 are denoted in FIGS. 10, 16 and 18 with an asterisk.

EXAMPLE 4

Stimulation of Locomotor Activity in Mice by Compound 2 Lasts Up to Seven Hours

Cocaine Alone Study

Figure 19:
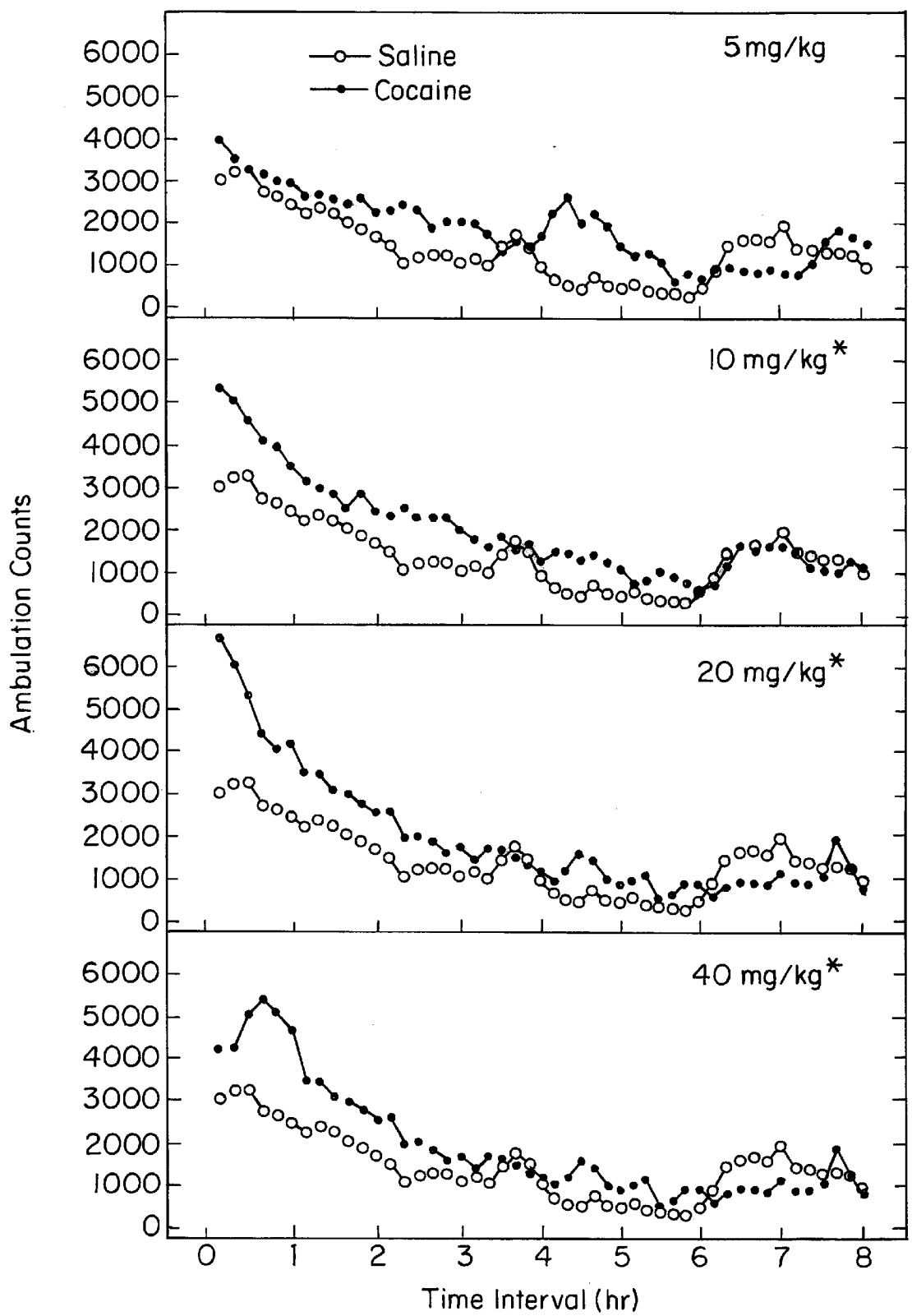
FIG. 19 is a graph showing the effect on mice of 1) 5 mg/kg, 2) 10 mg/kg, 3) 20 mg/kg and 4) 40 mg/kg of cocaine compared with saline on horizontal activity counts/10 minute over an eight hour session.

A dose response study of induced locomotor stimulation was conducted according to the following procedure. The study was conducted using 16 Digiscan locomotor activity testing chambers (40.5×40.5×30.5 cm) housed in sets of two, within sound-attenuating chambers. A panel of infrared beams (16 beams) and corresponding photodetectors were located in the horizontal direction along the sides of each activity chamber. A 7.5-W incandescent light above each chamber provided dim illumination. Fans provided an 80-dB ambient noise level within the chamber. Separate groups of 8 non-habituated male Swiss-Webster mice (Hsd:ND4, aged 2–3 months) were injected via the intraperitoneal (IP) route with either vehicle (0.9% saline) or test compound (5, 10, 20 or 40 mg/kg), immediately prior to locomotor activity testing. In all studies, horizontal activity (interruption of photocell beams) was measured for 8 hours within 10 minute periods, beginning at 0880 hours )two hours after lights on). Testing was conducted with one mouse per activity chamber FIG. 19 shows average horizontal activity counts/10 min as a function of time (0–8 hr) and dose of cocaine (top to bottom panels). Treatment with cocaine resulted in time-dependent stimulation of locomotor activity in doses from 10 to 40 mg/kg. Stimulant effects of 10, 20 and 40 mg/kg occurred within 10 minutes following injection and lasted up to 3 hours. Maximal stimulant effects were evident during the first 30 minutes following 20 mg/kg cocaine, and this period was selected for analysis of dose-response data. Using TableCurve 2D v2.03 software (Jandel Scientific), the mean average horizontal activity counts for this 30-min period were fit to a 3-parameter logistic peak function of $log_{10}$ dose (with the constant set to 3172, the mean of the saline-treated group), and the maximum was estimated from the resulting curve (maximum=6059 counts/10 min at 18.3 mg/kg). The $ED_{50}$ (dose producing one half maximal stimulant activity) was estimated at 8.8 mg/kg from a linear regression against $log_{10}$ dose of the ascending portion of the dose-effect curve (5–20 mg/kg cocaine).

A two-way analysis of variance conducted on horizontal activity counts/10 min indicated a significant interaction of Treatment with 10-Minute Periods, as well as a main effect of 10-Minute Periods (ps<0.001). The main effect of Treatment was not significant in the two-way analysis, $F(4,35)=$ 2.2, p=0.089. A one-way analysis of variance conducted on $log_{10}$ horizontal activity counts for the 0–30 min time period (maximal stimulant effect) indicated a significant effect of Treatment $F(4,35)=9.1$, p<0.001, and planned comparisons (a priori contrast) against the vehicle group showed a significant difference for 10, 20 and 40 mg/kg (all ps<0.05 denoted on FIG. 19 with an asterisk).

Compound 2 Alone Study

A time course study of Compound 2-induced locomotor stimulation was conducted under the same conditions as outlined above for the cocaine alone study described above. Separate groups of eight mice were injected with either vehicle (deionized water) or Compound 2 (1, 3, 10 pr 30 mg/kg) immediately prior to locomotor activity testing.

Figure 20:
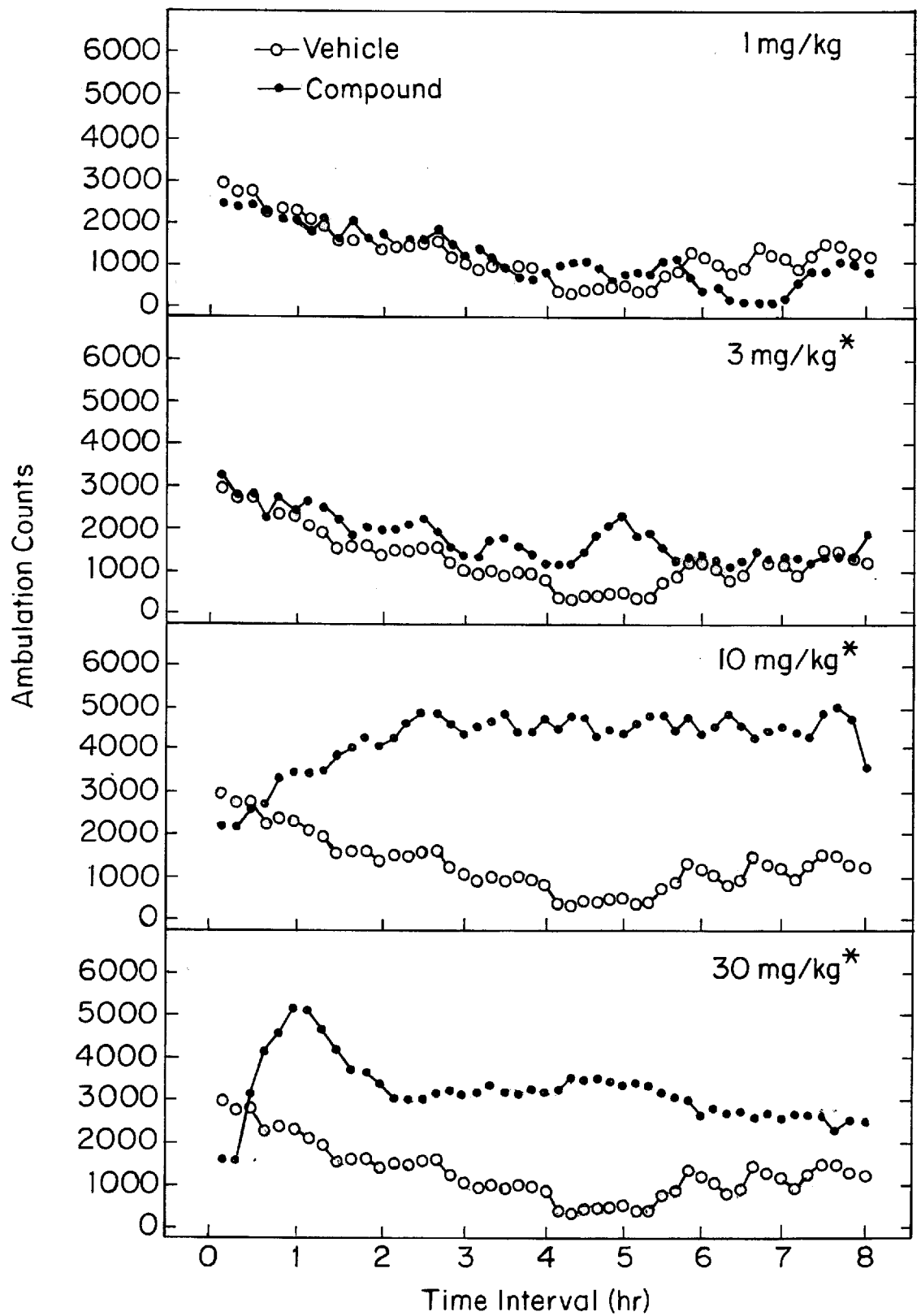
FIG. 20 is a graph showing the effect on mice of 1) 1 mg/kg, 2) 3 mg/kg, 3) 10 mg/kg and 4) 30 mg/kg of Compound 2 compared with saline on horizontal activity counts/10 minute over an eight hour session.

FIG. 20 shows average horizontal activity counts/10 min as a function of time (0–8 hr) and dose of Compound 2 (top to bottom panels). Treatment with Compound 2 resulted in time-dependent stimulation of locomotor activity in doses from 3 to 30 mg/kg. Stimulant effects occurred within 40 to 70 minutes following injection and lasted 4 to $\geq 7$ hours. The time period 280–310 min was selected for analysis of dose-response data because this was the time period in which maximal stimulant effects first appeared as a function of dose. Using TableCurve 2D v2.03 software (Jandel Scientific), the mean average horizontal activity counts/10 min for this period were fit to a 3-parameter logistic peak function of $log_{10}$ dose (with the constant set to 399, the mean of the vehicle-treated group), and the maximum effect estimated from the resulting curve (maximum=4581 counts/ 10 min at 12.9 mg/kg) . The $ED_{50}$ (dose producing one half maximal stimulant activity) was estimated at 3.3 mg/kg from a linear regression against $log_{10}$ dose of the ascending portion of the dose-effect curve (1 to 10 mg/kg 30,644). The maximal effect/cocaine maximal effect ratio (ME/CME) was equal to 1.4 based upon the cocaine dose-effect data determined described above.

A two-way analysis of variance conducted on horizontal activity counts/10 min indicated significant effects of Treatment $F(4,35)=21.5$, p<0.001, 10-Minute Periods $F(47,1645)$ =5.9, p<0.001, and the interaction of those factors $F(188, 1645)=4.5$, p<0.001. A one-way analysis of variance conducted on $log_{10}$ horizontal activity counts for the 280–310 min time period (maximal stimulant effect) indicated a significant effect of Treatment $F(4,35)=21.3$, p<0.001, and planned comparisons (a priori contrast) against the vehicle group showed a significant difference for 3, 10 and 30 mg/kg (all ps<0.05 denoted on FIG. 20 with an asterisk).

EXAMPLE 5

Binding of Indamines to the Dopamine (DA), Serotonin (5HT) and Norepinephrine (NE) Cloned Transporter and Inhibition of Dopamine, Serotonin and Norepinephrine Uptake Compounds were tested for their effects on radioligand ($[^{125}I]$)RTI-55) binding to and [$^3$H]dopamine uptake by C6 cells expressing cDNA for the human dopamine transporter (C6-hDAT cells), their effects on radioligand ($[^{125}I]$)RTI-55) binding and [$^3$H]serotonin uptake by HEK cells expressing cDNA for the human serotonin transporter (HEK-hSERT cells), and its effects on radioligand ($[^{125}I]$)RTI-55) binding and [$^3$H]norepinephrine uptake by HEK cells expressing cDNA for the human norepinephrine transporter (HEK-hNET cells).

Drugs (10 mM stock solution) were dissolved in DMSO. The final DMSO concentration in the assay is 0.01 percent. Pipetting was performed with a Biomek 2000 robotic work station.

([$^{125}$I])RTI-55) Binding

Prep: Cells were grown on 150 mm diameter tissue culture dishes. Medium was poured off the plate, the plate was washed with 10 ml of phosphate buffered saline, and 10 ml of lysis buffer (2 mM HEPES, 1 mM EDTA) was added. After 10 minutes, cells were scraped from plates and poured into centrifuge tubes and centrifuged for 20 minutes at 30,000×g. Supernatant was removed, and the pellet was resuspended in 20–32 ml 0.32M sucrose, depending on the density of binding sites in a given cell line (i.e., a resuspension volume which results in binding <10% of the total radioactivity), with a Polytron at setting 7 for 10 seconds.

Assay: Each assay contained 50 μl membrane preparation (approximately 15 μg protein), 25 μl of drug, and 25 μl of [$^{125}$I]RTI-55 (40–80 μM final concentration) in a final volume of 250 μl. Krebs HEPES was used for all assays. Membranes were preincubated with drugs for 10 minutes prior to addition of [$^{125}$I]RTI-55. The reaction was incubated for 90 minutes at room temperature in the dark and was terminated by filtration onto GF/C filters using a Tom-tech harvester. Scintillation fluid (50 μl) was added to each square and radioactivity remaining on the filter was determined using a Wallac β-plate reader. Competition experiments were conducted with duplicate determinations. Data was analyzed using GraphPAD Prism, with IC$_{50}$ values were converted to K$_1$ values using the Cheng-Prusoff equation.

cells were allowed to set for 15 minutes, and radioactivity in the TCA was determined by conventional liquid scintillation spectrometry.

[$^{3}$H]Neurotransmitter Uptake for HEK-HSERT and HEK-HNET Cells: Filtration Assay HEK-hSERT or HEK-hNET cells were plated on 150 mm dishes and grown till confluent. The medium was removed, and cells were washed twice with room temperature phosphate buffered saline (PBS). Following addition of PBS (3 ml), the plates were placed in a 25° C. water bath for 5 minutes. The cells were gently scraped and then triturated with a pipette. Cells from multiple plates were combined. One plate provided enough cells for 48 wells which tested two drug curves.

The assay was conducted in 961 ml vials and used the Tomtech Harvester and Betaplate reader. Krebs HEPES (350 μl) and drug solution (50 μl) were added to vials and placed in a 25° C. water bath. Cells (50 μl) were added, preincubated for 10 minutes, and [$^{3}$H]5HT or [$^{3}$H]NE (50 μl, 20 nM final concentration) was added. Uptake was terminated after 10 minutes by filtration on the Tomtech Harvester using filters presoaked in 0.05% polyethylenimine. The 10 minute uptake time was at the upper edge of the linear time course to obtain a sufficient number of specific counts. The number of cells per assay could not be increased due to the limitation of clogging the filter.

The results for Compound 1–10 are shown below in Table II.

TABLE II

Binding to DA, 5HT and NE Cloned Transporters (K$_i$; nM) and Inhibition of DA, 5HT and NE Uptake (IC$_{50}$; nM)

| | DA | | | 5HT | | | NE | | | | |
|---|---|---|---|---|---|---|---|---|---|---|---|
| Compound | [I$^{125}$]RTI$^{-55}$ | uptake | uptake/binding | [I$^{125}$]RT$^{I-55}$ | uptake | uptake/binding | [I$^{125}$]RT$^{I-55}$ | uptake | uptake/binding | 5HT/DA uptake | NE/DA uptake |
| cocaine | 300 ± 10 | 330 ± 30 | 1.1 | 500 ± 50 | 310 ± 40 | 0.62 | 2700 ± 350 | 190 ± 50 | 0.07 | 0.94 | 0.58 |
| indanamines | | | | | | | | | | | |
| 4 | 8.1 ± 1.3 | 61 ± 12 | 7.5 | 2.0 ± 0.8 | 13 ± 4 | 6.5 | 48 ± 29 | 28 ± 14 | 0.58 | 0.21 | 0.46 |
| 5 | 27 ± 6 | 23 ± 10 | 0.85 | 5.0 ± 0.8 | 4.8 ± 1.5 | 0.96 | | | | 0.21 | |
| 1 | 29 ± 6 | 190 ± 20 | 6.6 | 3.1 ± 1.2 | 6.7 ± 2.2 | 2.2 | 370 ± 60 | 72 ± 40 | 0.19 | 0.035 | 0.38 |
| 8 | 220 ± 40 | 53 ± 1 | 0.24 | | | | | | | | |
| 2 | 250 ± 30 | 340 ± 10 | 1.4 | 91 ± 9 | 190 ± 40 | 2.1 | 400 ± 100 | 640 ± 330 | 1.6 | 0.56 | 1.9 |
| 3 | 39 ± 7 | 270 ± 30 | 6.9 | 16 ± 0.8 | 24 ± 7 | 1.5 | | | | 0.10 | |
| 9 | 32 ± 6 | 51 ± 21 | 1.6 | 93 ± 9 | 240 ± 70 | 2.6 | 110 ± 50 | 75 ± 35 | 0.68 | 4.7 | 1.5 |
| 2 | 180 ± 100 | 190 ± 60 | 1.1 | 44 ± 6 | 1500 ± 500 | 34. | 260 ± 80 | 420 ± 220 | 1.6 | 7.9 | 2.2 |
| 10 | 120 ± 3 | 550 ± 200 | 4.6 | 180 ± 45 | 3700 ± 1300 | 21. | 2800 ± 1900 | 1600 ± 240 | 0.57 | 6.7 | 2.9 |
| 6 | 130 ± 90 | 370 ± 170 | 2.8 | 740 ± 260 | 3100 ± 1200 | 4.2 | 150 ± 50 | 310 ± 50 | 2.1 | 8.4 | 0.84 |
| 7 | 890 ± 280 | 2700 ± 1500 | 3.0 | 4700 ± 300 | >10 μM | | 440 ± 80 | 1000 ± 400 | 2.3 | | 0.37 |

[$^{3}$H]Neurotransmitter Uptake for C6 HDAT Cells

For experiments involving uptake of [$^{3}$H]DA, the medium was removed and Krebs HEPES buffer (25 mM HEPES, 122 mM NaCl, 5 mM KCl, 1.2 mM MgSO$_4$, 2.5 mM, CaCl$_2$, 1 μM pargyline, 0.2 g glucose/100 ml, 0.02 g ascorbic acid/ 100 ml, pH 7.4) was added. Uptake was initiated with the addition of [3H]DA (20 nM, specific acitivity 20–53 Ci/mmol) in a final volume of 500 μl. Mazindol (5 μM) was used to define nonspecific uptake. Cells were preincubated for 10 minutes, with drug before addition of neurotransmitter. Uptake was terminated after a 2 minute incubation by removing buffer, and the plate was placed on ice and washed twice with 1 ml ice cold phosphate-buffered saline. Trichloroacetic acid (TCA, 0.5 ml, 3%) was added to each well,

EQUIVALENTS

Those skilled in the art will know, or be able to ascertain using no more than routine experimentation, many equivalents to the specific embodiments of the invention described herein. These and all other equivalents are intended to be encompassed by the following claims.

What is claimed is:

1. A compound represented by the following structural formula:

17

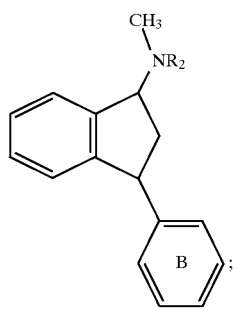

wherein

R2 is n-propyl, iso-propyl, n-butyl, sec-butyl, or tert-butyl; and

Ring B is unsubstituted or substituted with one, two or three substituents.

2. The compound of claim 1 wherein the compound has the trans sterochemistry.

3. The compound of claim 2 wherein the compound is represented by the following structural formula:

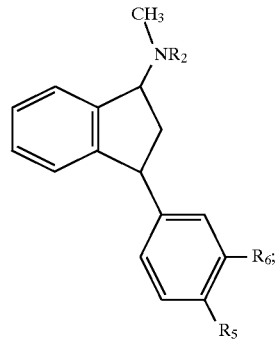

18 wherein:

R2 is n-propyl, iso-propyl, n-butyl, sec-butyl, or tert-butyl; and

R5 and R6 are independently selected from the group consisting of —H, halogen, an alkyl group, a substituted alkyl group, hydroxy, (lower alkyl)—O—, (substituted lower alkyl)—O—, —CN, —NO$_2$, amine, (lower alkyl) amine, (substituted lower alkyl) amine, (di-lower alkyl) amine and (substituted di-lower alkyl) amine.

4. The compound of claim 3 wherein R2 is n-propyl.

5. The compound of claim 4 wherein R5 and R6 are each —Cl.

6. The compound of claim 2 wherein R2 is n-butyl, sec-butyl or t-butyl.

7. The compound of claim 6 wherein R5 and R6 are each —Cl.

8. A compound represented by the following structural formula:

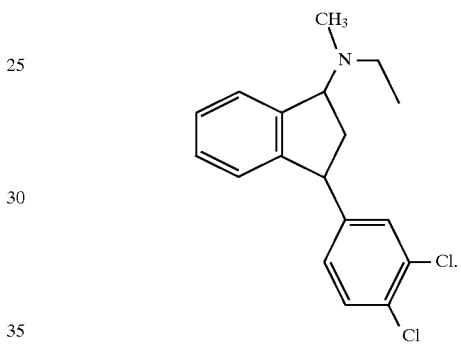

* * * * *